United States Patent [19]

McCormick et al.

[11] Patent Number: 5,441,613
[45] Date of Patent: Aug. 15, 1995

[54] METHODS AND APPARATUS FOR REAL-TIME MONITORING, MEASUREMENT AND CONTROL OF ELECTROOSMOTIC FLOW

[75] Inventors: Randy M. McCormick, Santa Clara; Roy D. Rocklin, Sunnyvale, both of Calif.

[73] Assignee: Dionex Corporation, Sunnyvale, Calif.

[21] Appl. No.: 161,942

[22] Filed: Dec. 3, 1993

[51] Int. Cl.$^6$ .................... G01N 27/26; G01N 27/447
[52] U.S. Cl. ......................... 204/180.1; 204/299 R
[58] Field of Search .................. 204/299 R, 180.1

[56] References Cited

U.S. PATENT DOCUMENTS

| | | | |
|---|---|---|---|
| 4,908,116 | 3/1990 | Zare et al. | 204/180.1 X |
| 5,009,760 | 4/1991 | Zare et al. | 204/299 R X |
| 5,092,972 | 3/1992 | Ghowsi | 204/299 R X |
| 5,151,164 | 9/1992 | Blanchard et al. | 204/299 R X |
| 5,169,510 | 12/1992 | Lunte et al. | 204/180.1 X |
| 5,180,475 | 1/1993 | Young et al. | 204/180.1 |
| 5,181,999 | 1/1993 | Wiktorowicz | 204/180.1 |

OTHER PUBLICATIONS

Bart J. Wanders, Tom A. A. van de Goor, and Frans M. Everaerts, "On-line measurement of electroosmosis in capillary electrophoresis using a conductivity cell" Journal of Chromatography A, vol. 652 No. 1 (15 Oct. 1993) 291–294.
W. T. Kok and Y. Sahin "Solid-State Field Decoupler for Off-Column Detection in Capillary Electrophoresis" Anal. Chemistry (Sep. 1993) 65 2497–2502.
Cheng S. Lee et al "Factors Affecting Direct Control of Electroosmosis Using An External Electric Field on Capillary Electrophoresis" Anal. Chemistry (Aug. 1991) 63 1519–1523.
Manabu Miyamoto et al "Electro-Osmotic Flow Measurements" Journal Membrane Science (1989) 41 377–391.
J. C. Reijenga et al "Effect of Electroosmosis on Detection in Isotachophoresis"Journal of Chromatography (1983) 241–254.
B. J. Wanders et al "Methods for On-Line Determination and Control of Electroendosmosis in Capillary Electrochromatography and Electrophoresis" J. Chromatography (1989) 470 89–93.
T. Wang et al "Capillary modification and evaluation using streaming potential and frontal chromatography for protein analysis in capillary electrophoresis" J. Chromatog. 592 (1992) 325–334.

Primary Examiner—Kathryn Gorgos
Assistant Examiner—John S. Starsiak, Jr.
Attorney, Agent, or Firm—Flehr, Hohbach, Test, Albritton & Herbert

[57] ABSTRACT

In capillary electrophoresis systems, real-time monitoring and measurement of the electroosmotic flow through a separation capillary is accomplished by coupling the outlet of the separation capillary to an electrically-conductive junction. In one embodiment, this junction is an ion-impermeable or an ion-exchange membrane unit that preferentially exchanges ions having a charge opposite to analyte ions of interest. Within a downstream region of the junction, all axial incremental voltage from the electroosmotic voltage source is terminated, which ensures that downstream electrolyte ion movement is passive, due to active flow created upstream when an incremental axial voltage existed. Upstream electrolyte ion flux is proportional to $C_1 \cdot (\mu_e + \mu_{eo})$, where $C_1$ is the upstream concentration of the electrolyte ion of interest, $\mu_e$ is the electrolyte electrophoretic mobility, and $\mu_{eo}$ is the electroosmotic mobility. Downstream, the flux is proportional to $C_2 \cdot \mu_{eo}$, where $C_2$ is the downstream concentration of the electrolyte ion of interest. The fluxes are equal, whereupon $\mu_{eo} \approx C_1 \cdot \mu_e / (C_2 - C_1)$. Since $\mu_e$ is known, $\mu_{eo}$ can be determined in real-time by measuring $C_2$ and $C_1$. In a second embodiment, the electrically-conductive junction preferably is a grounding capillary that converts plug-like electroosmotic flow to parabolic flow. A parabolic flow characteristic such as streaming potential, streaming current, or pressure differential is measured in real-time to ascertain electroosmotic flow rate. In each embodiment, the realtime measured flow information is feedback-coupled to preferably alter zeta-potential to regulate electrolyte solution flow in the separation capillary.

29 Claims, 13 Drawing Sheets

METHODS AND APPARATUS FOR REAL-TIME MONITORING, MEASUREMENT AND CONTROL OF ELECTROOSMOTIC FLOW

FIELD OF THE INVENTION

The invention relates to capillary electrophoretic measurements, and more particularly to methods and devices that monitor electroosmotic flow in real-time, generate a signal proportional to electroosmotic flow magnitude, and use such signal to control, alter and/or quantitate electroosmotic flow.

BACKGROUND OF THE INVENTION

Capillary electrophoresis is an analytical tool wherein analyte ions in an electrolyte solution are separated using an electric field. A source of voltage is coupled between the input (or source) and output (or destination) ends of a narrow bore capillary containing the electrolyte solution. The voltage source establishes a voltage gradient axially along the capillary that causes axial migration of ions within the capillary.

Typically the capillary is made from silica, a material that forms fixed negative charges on the inner capillary wall in the presence of an electrolyte solution. Even before the voltage gradient is applied, cations in the electrolyte solution will be attracted to these fixed negative charges, forming a so-called double layer at the capillary wall. Because they are negatively charged, electrolyte anions will be repelled from the capillary wall.

In a commonly used mode of operation, the voltage gradient is applied such that the source end of the capillary is positive relative to the destination end. Electrolyte cations are attracted both to the negatively charged capillary wall and to the capillary end coupled to the negative end of the voltage gradient. Conversely, electrolyte anions are repelled from the capillary wall and are attracted to the capillary end coupled to the positive end of the voltage gradient.

The voltage gradient will create a net movement of the cations loosely associated with the fixed negative charges at the electrolyte/silica interface, which movement drags the bulk of the electrolyte solution toward the negatively charged capillary destination end. This net bulk flow towards one capillary end is termed electroendosmotic or electroosmotic flow and has a characteristic plug-like velocity profile radially across the capillary. By plug-like, it is meant that a radial cross-section of the flow will exhibit uniform velocity everywhere.

The bulk electrolyte solution movement occurs at a rate proportional to electroosmotic mobility, $\mu_{eo}$. Generally, mobility is the per unit time rate of movement toward a charge, normalized for the magnitude of the imposed electrical field that induces the movement. Electroosmotic flow is further characterized by the absence of an axial pressure differential across the capillary through which the flow is occurring.

As cations subjected to the voltage gradient cause the electrolyte solution to move axially along the capillary length due to electroosmotic flow, variously charged analyte ions that might be present within the electrolyte solution are subjected to electrophoresis. Electrophoresis is the movement of analyte ions in an axial direction, toward an electrode of opposite charge or away from an electrode of like charge at the capillary ends.

The rate of electrophoretic movement is influenced by the axial voltage gradient (i.e. the electrical field strength) imposed across the length of the capillary through the electrolyte solution, and by the analyte electrophoretic mobility, $\mu_a$. Analyte electrophoretic mobility is the per unit time rate of axial movement of an ion per unit electrical field strength toward or away from appropriately charged electrodes. The rate of electrophoretic movement is defined in the absence of any electroosmotic flow.

Analyte ions within the electrolyte solution migrate differentially based upon their electrophoretic mobilities. If, for example, the rate of the electroosmotic flow exceeds the rate of electrophoretic movement of anions, all of the analyte ions are moved axially in the direction of the electroosmotic flow, but at different rates. In a capillary with a negatively-charged inner wall, anions tend to move in a direction opposite to the electroosmotic flow, but may be swept along in the direction of the prevailing electroosmotic flow. By contrast, cations move in the same direction as the electroosmotic flow and thus are swept along more rapidly than anions. Neutral species are carried along solely by the electroosmotic flow and migrate together as a band situated after the faster-moving cation bands but before slower-moving anion bands.

In another mode of operation, it is also possible to reverse the negative charge on the capillary wall by suitably modifying the silica wall such that fixed positive charges are present. In this mode, anions in the electrolyte are attracted to the charged wall, again forming an electrical double layer. Electrolyte anions then move toward the positive end of the electric field, which is coupled to the destination end of the capillary. In this mode, the anions migrate in the same direction as the bulk electroosmotic flow.

In either mode, for ease of analysis it is desirable that an analyte traverse the capillary length at a constant reproducible time, the so-called migration time. A constant migration time for a given set of conditions (e.g., electrolyte solution composition, pH, concentration, temperature, and electric field strength) simplifies analysis since analyte peak areas need not be corrected for migration time differences. Further, computerized peak identification of analytes is dependent upon relatively little or no change in migration times in sequential separations of standards and unknown samples.

Migration time depends upon the velocity of the analyte relative to the inner capillary wall, e.g., the net velocity of the analyte. Within the capillary, net analyte velocity represents the product of the electric field strength E multiplied by the sum of the analyte mobility $\mu_a$ for each analyte species and the electroosmotic mobility $\mu_{eo}$.

While analyte mobility $\mu_a$ is invariant for a given set of conditions, electroosmotic mobility $\mu_{eo}$ is dependent upon the potential appearing at the surface of the inner capillary wall, the so-called zeta potential. The zeta potential can vary with time as slow chemical changes take place at the capillary surface. For example, reequilibration of the capillary after cleaning, adsorption of contaminant molecules, and slow desorption of contaminant molecules from the capillary wall can affect the zeta potential, thus affecting electroosmotic mobility, $\mu_{eo}$.

If the electroosmotic mobility or flow can be measured and controlled, a constant analyte migration time and simplified analysis can result. Furthermore, control of electroosmotic flow can be used to optimize separation of mixtures of analyte molecules by permitting adjustment of migration times. For example, slowing flow during the separation of high-mobility analytes will permit a longer time period to achieve better separation of analyte molecules with similar electrophoretic mobility values.

Electroosmotic flow measurement and control requires measurement of the instantaneous electroosmotic mobility or flow, whereupon the electroosmotic mobility may be adjusted to restore its original value. If the instantaneous electroosmotic flow ate is known, it may be suitably adjusted to provide the desired constant analyte migration time. As used herein, the terms electroosmotic flow and electroosmotic mobility will be used interchangeably. This interchangeability of terms is justified since electroosmotic flow=(electroosmotic mobility)·(electrical field strength)·(cross-sectional capillary area).

Measurement of the electroosmotic flow may be used to gauge the state of the separation capillary, as the flow directly reflects the extent of contamination or change of the charge layer on the capillary wall. Electroosmotic flow also can serve as an internal reference for expressing a migration parameter for analyte species, analogous to the way the dead time or dead volume is used to derive capacity factor k' in chromatographic separations.

Various techniques are practiced in the prior art to determine electroosmotic flow. It is known to use an electrically neutral flow marker to measure electroosmotic flow, see for example, T. S. Stevens and H. J. Cortes, Analytical Chemistry (1983) 55 1365–1370; K. D. Lukacs and J. W. Jorgenson, J. High Resolut. Chromatogr. Chromatogr. Commun (1985) 8 407; J. E. Wiktorowicz, U.S. Pat. Nos. 5,181,999 and 5,015,350. Hanai et al. (J. High Resolut. Chromatogr. Chromatogr. Commun. (1991) 14 483) disclosed the use of a number of neutral flow markers for the determination of electroosmotic flow rates in capillary electrophoresis. In addition, Lee et al. (J. Chromatogr. (1991) 559 122–140) described the use of a UV marker that was injected into the capillary to monitor changes in electroosmotic flow induced by application of an external electrical field.

However, it is difficult to find a neutral marker species readily soluble in aqueous solutions that has the requisite spectral characteristics to render it detectable by conventional capillary electrophoresis ("CE") detection technology. The marker must be truly neutral under all pH conditions, and must not adsorb or partition onto the capillary wall. The UV marker method permits only one measurement of the electroosmotic flow during each electrophoretic separation, and is not a continuous, realtime measurement method.

While the use of multiple series-connected conductivity detectors to measure analyte mobility $\mu_a$ is known, such technique cannot measure electroosmotic mobility $\mu_{eo}$. See J. L. Beckers, Th. P. E. M. Vergeggen, F. M. Everaerts, J. Chromatogr. (1988) 452 591–600.

Another prior art approach measures electroosmotic flow by measuring changes in electrical current flowing through the capillary as electroosmotic flow displaces the electrolyte solution therein with an electrolyte solution of slightly different composition. See, for example, Huang, Gordon, and Zare, Analytical Chemistry (1988) 60 1837–1838. In Analytical Chemistry (1991) 63 1519–1523, Lee, et al. describe the use of the above-described current-monitoring method to monitor changes in electroosmotic flow induced in a separation capillary by application of an external electric field.

However, this "off-line" current-monitoring technique does not permit real-time measurements, e.g., measurements made contemporaneously during actual separation of analyte ions. Further, this prior art measurement technique will by necessity change the chemical composition of the electrolyte solution in the capillary. As such, this technique interferes with the accuracy of the measurement of the magnitude of electroosmotic flow, which is a function of both the ionic strength and the chemical composition of the electrolyte solution.

Measuring the time required for a change in electrolyte solution concentration to reach the detector has also been used to determine electroosmotic mobility $\mu_{eo}$; see, for example U.S. Pat. No. 5,009,760 to Zare. However, as noted, such measurements are not accurate in that the electrolyte solution is changed during the measurement process. Further, such measurements do not provide the instantaneous electroosmotic flow rate measurement required to allow rapid flow rate adjustment.

Yet another prior art technique requires the periodic weighing or volumetric determination of the quantity of effluent electrolyte solution from the capillary. The electroosmotic flow rate is estimated from the mass flow rate of the electrolyte. This technique is described by Altria and Simpson, Analytical Proceedings (1986) 23 453 and B. J. Wanders, A. A. A. M. Van de Goor, and F. M. Everaerts, J. Chromatogr. (1989) 470 89–93. Van de Goor et al. subsequently teach the use of on-line weighing of the effluent from the separation capillary as a method of deriving knowledge of the electroosmotic flow rate through the capillary (A. A. A. M. Van de Goor, B. J. Wanders, and F. M. Everaerts, J. Chromatogr. (1989) 95–104). However, measurements of instantaneous electroosmotic flow were not possible as readings could be taken only every 5 minutes.

Lee and Hong (J. Membrane Sci. (1988) 39 79–88) have described a device for measurement of electroosmotic flow through microporous membranes. The Lee-Hong device is based on measurement of the volume of liquid pumped out of an overflow channel from a chamber into which fluid is being pumped via electroosmotic flow. The volume of fluid pumped out of the overflow channel as a function of time is a measure of the magnitude of rate of electroosmotic flow of fluid into the chamber. Generally, however, such measurements cannot be conducted in real-time during an actual separation of the analyte ions with sufficient frequency as to permit control of the electroosmotic flow during the separation.

Van de Goor et al. also teach the use of off-line measurements of streaming potential to observe changes in the capillary with time. Similarly, Wang and Hartwick (J. Chromatogr. 594 1992 325–334) and Reijenga et al. (J. Chromatogr 260 (1983) 241–254) teach the use of streaming potential measurement for characterization of the capillary wall in contact with various electrolyte solutions. No real-time, on-line measurement of electroosmotic flow through a separation capillary was discussed by either reference.

One real-time, on-line prior art approach to monitoring electroosmotic flow introduces a hydrostatically-driven liquid stream containing an ultraviolet-absorbing species into the electroosmotically-moved electrolyte solution from the separation capillary. Under constant electroosmotic flow and hydrostatic flow conditions, a combined effluent stream of constant ultraviolet absorptivity results. Electroosmotic flow rate variations produce changes in the concentration of the ultraviolet-absorbing tracer species in the combined effluent stream. Real-time electroosmotic flow data can be obtained, permitting use of feedback to control electroosmotic mobility by changing the magnitude of the axial voltage gradient along the separation capillary such that migration times are made more constant; see Wanders, Van de Goor, and Everaerts, J. Chromatogr. (1989) 470 89–93.

Understandably, providing a suitable mechanism for combining the two streams and sensing ultraviolet concentration complicates the measurement process. In addition, changes in the hydrostatically-driven flow of UV absorbing tracer as well as a change in the electroosmotic flow rate can result in a change in the spectral absorbance of the combined stream of effluent. Finally, though this approach can vary electroosmotic flow by changing the axial voltage gradient along the capillary, the approach is of moderate value in practice. Variation of the axial voltage gradient produces analyte electrophoretic velocity changes concomitant with changes in the electroosmotic velocity.

Finally, in a scientific field unrelated to capillary electrophoresis, Miyamoto, et al., J. Membrane Sci (1989) 41 377–391, describe measurement of electroosmotic flow through sections of frog skin and gastric mucosa membranes. Miyamoto measured electroosmotic flow using a photodiode positioned along the overflow channel from a chamber into which fluid was pumped electroosmotically. Use of a pressure transducer to measure the flow indirectly was also described, wherein fluid pressure drop along the channel due to fluid flow into the chamber was measured.

The majority of the above-mentioned measuring methods are not readily amenable to on-line measurement of electroosmotic flow through separation capillaries. These prior art methods either do not provide a continuous, instantaneous measurement (e.g., use of a neutral flow marker) or they perturb the electroosmotic flow in the measurement process (e.g., measurement of the rate of change of a different buffer electroosmotically-pumped into the capillary).

What is needed is an on-line, real-time method and apparatus for monitoring and measuring electroosmotic flow that do not alter the electrolyte solution under measurement, and that do not impose substantial hardware overhead. Preferably such method and apparatus should produce a signal proportional to the magnitude of the electroosmotic flow, which signal may be used (manually or in a feedback loop) to adjust conditions such that electroosmotic flow can be made constant or changed in a predictable manner.

The present invention discloses such methods and apparatus.

SUMMARY OF THE INVENTION

As noted, in a conventional capillary electrophoresis separation system, a bulk solution with electrolyte ions therein is caused to move electroosmotically along a separation capillary. A source of voltage is coupled between the capillary input and output ends to produce an incremental axial voltage along the separation capillary length. It is this incremental axial voltage that produces electroosmotic, plug-like movement of the bulk electrolyte and, consequently, of the analyte ions therein.

The present invention provides an electrically-conductive junction and flow detection mechanism downstream from the separation capillary output end. The electrically-conductive junction couples the separation capillary and the flow detection means, and facilitates real-time monitoring and measurement of electroosmotic flow. The electrically-conductive junction terminates the high voltage associated with the electrical field across the separation capillary and permits transport of electroosmotically-moved fluid between the separation capillary and the flow detection means.

In a first embodiment, the electrically-conductive junction is either an ion-impermeable or an ion-exchange membrane unit series-coupled with the electroosmotic flow and the separation capillary to define a channel having upstream and downstream regions between the separation capillary and the flow detection means.

The ion-exchange membrane unit preferably is surrounded by an electrolyte solution and preferentially exchanges an ion type that is opposite in charge to the analyte ions of interest (which may be anions or cations) within the bulk electrolyte solution within the separation capillary. The ion-impermeable unit prohibits exchange of both anions and cations. The bulk electrolyte solution and analyte ions therein flow from the separation capillary into the upstream region of the conductive-junction channel, and bulk solution and non-exchanged ions flow through the downstream region.

Preferably the conductive-junction is sized such that by at least the downstream region thereof, the axial electroosmotic-flow-producing voltage drop in the separation capillary is eliminated. As a result, in the downstream region the bulk electrolyte solution and all analyte ions in that solution are passively swept along axially by the electroosmotic force upstream.

As in conventional electrophoresis separation, the anion of the bulk electrolyte solution is actively moved axially along a separation capillary. This active movement results from an axial incremental voltage produced by a source of voltage coupled between the input and output of the separation path. An electrolyte anion actively moved in this fashion will have a flux proportional to the product of its concentration ("$C_1$") and the sum of the electroosmotic "$\mu_{eo}$" and anion electrophoretic mobilities "$\mu_e$", specifically $C_1 \cdot (\mu_{eo} + \mu_e)$.

In the first embodiment, downstream from the electrically-conductive junction, the passively moving non-exchanged electrolyte anion has a flux proportional to $C_2 \cdot \mu_{eo}$, where $C_2$ is the concentration of the electrolyte ions in the downstream region. In the series-configured channel provided, the upstream flux equals the flux at the downstream region. It therefore follows that $\mu_{eo} = -\mu_e \cdot C_1/(C_2 - C_1)$.

For a given set of conditions, the upstream electrolyte anion electrophoretic mobility will be known and constant. Thus, the first embodiment of the present invention determines electroosmotic mobility $\mu_{eo}$ in real time and on-line by monitoring bulk electrolyte solution concentrations upstream ($C_1$) and downstream ($C_2$). Since $C_1$ is substantially constant, it may be measured anywhere upstream from the conductive-junction unit, and in fact may be determined before a separation experiment is run. The $C_1$, $C_2$ data may be measured using any detection instrument that generates a signal proportional to electrolyte concentration.

In a second embodiment, the electrically-conductive junction transforms the electroosmotic plug-like flow from the separation capillary into a parabolic flow (also known as laminar or Poiseuille flow) that is equivalent in magnitude to the electroosmotic flow because of the series-coupled configuration of the embodiment. Because the flow at the downstream end of the electrically-conductive junction is parabolic, the parabolic flow-rate may be measured in many ways. The parabolic flow possesses several characteristics that are readily measured and that relate directly to the electroosmotic flow rate through the separation capillary. In this embodiment, a property associated with the parabolic flow is then determined in real-time by the flow detector apparatus, to provide a real-time measure of electroosmotic flow through the separation capillary.

In the second embodiment, the electrically-conductive junction and all points downstream are held at a fixed electrical potential, preferably ground potential. The fixed potential creates a constant incremental axial voltage along the electrically-conductive junction and at all points downstream thereof, which terminates the plug-like electroosmotic flow and converts it to parabolic flow. Preferably the electrically-conductive junction is a microporous capillary material surrounded by a conductive solution at ground potential.

After conversion from electroosmotic flow to parabolic flow occurs, a variety of detection mechanisms can monitor and measure electroosmotic flow in real-time. Because parabolic flow implies the existence of an axial pressure differential, differential pressure measurements along the flow detection means can determine electroosmotic flow. Further, if the parabolic flow traverses a charge-retaining conduit in the flow detection means, a streaming potential and/or streaming current is generated, the measurement of which provides a real-time measure of electroosmotic flow.

In each embodiment, the present invention provides a real-time knowledge of electroosmotic flow rate. This knowledge permits an experimenter to adjust flow through the separation capillary while the experiment is on-going. For example, the zeta potential at the inner wall of the separation capillary may be varied to alter the electroosmotic flow such that analyte migration times are made constant. Alternatively, the electroosmotic flow through the separation capillary may be augmented or counteracted with a hydrostatic flow derived by imposing a controlled pressure across the separation capillary. The measured electroosmotic mobility data may be provided as input to a feedback system that automatically regulates electroosmotic flow. Further, with proper calibration, the real-time signal provided by the present invention may be translated directly into a measurement of the magnitude of electroosmotic flow through the capillary.

Other features and advantages of the invention will appear from the following description in which the preferred embodiments have been set forth in detail, in conjunction with the accompanying drawings.

DETAILED DESCRIPTION OF THE PREFERRED EMBODIMENTS

Figure 1:
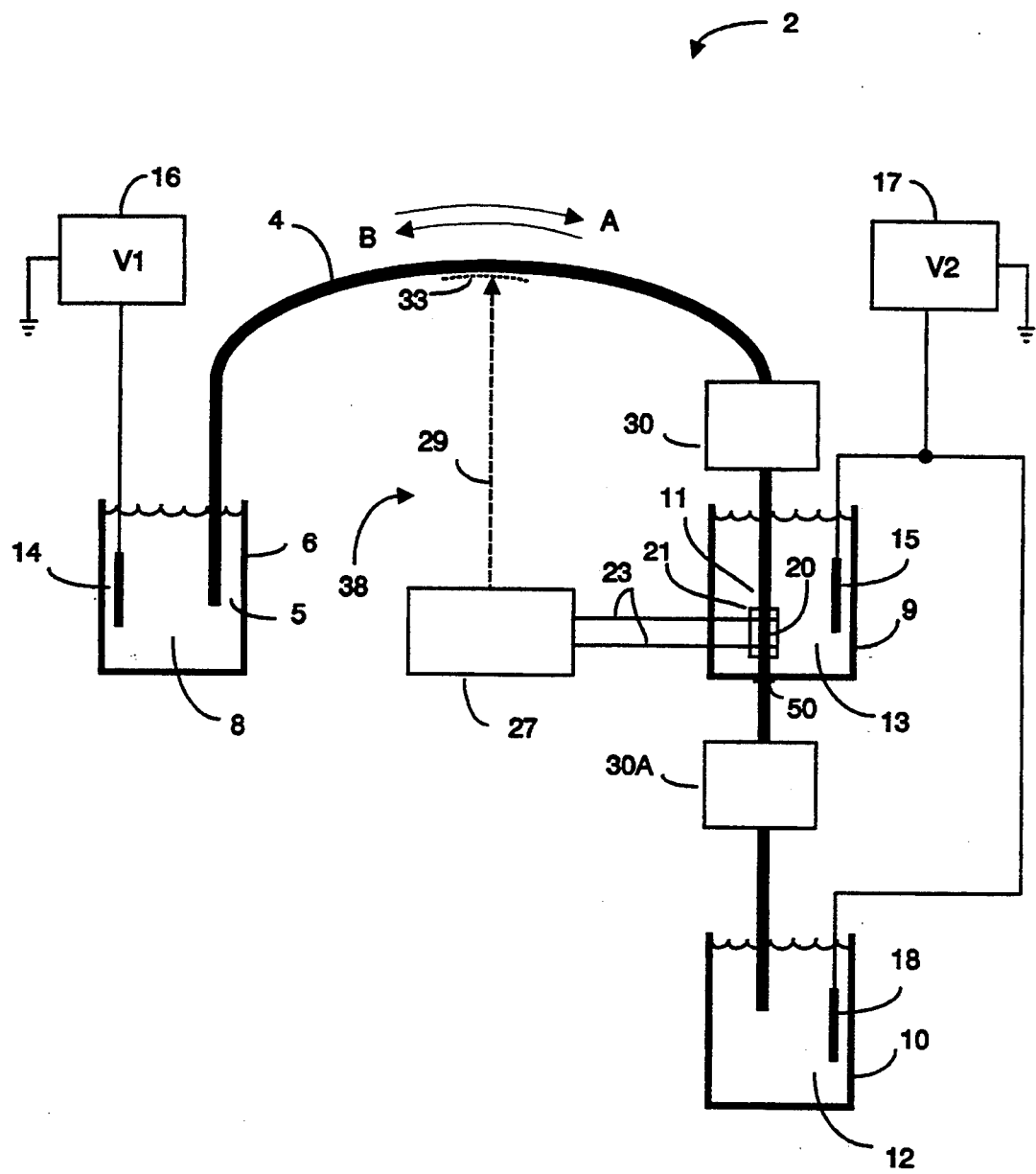
FIG. 1 depicts a generic system according to the present invention for real-time monitoring and measurement of electroosmotic flow, and further depicts generic feedback control of flow using real-time monitoring data.

FIG. 1 generically depicts a system 2 according to the present invention as including a conventional separation capillary 4 whose first or source end 5 is in fluid communication with a first or source container 6 holding a first electrolyte solution 8. The second or destination end 11 of separation capillary 4 is in fluid communication with an electrically-conductive junction 20 and with a second or destination container 10 holding a second electrolyte solution 12. Depending upon the specific embodiment used, preferably an intermediate container 9 holding a third electrolyte solution 13 may also be in electrical but not fluid communication with capillary 4 via electrically-conductive junction 20. As shown in FIG. 1, the electrically-conductive junction 20 is preferably disposed within the intermediate container 9. Preferably a gasket-like fitting 50 facilitates passage through the lower wall of container 9.

The terms "input" or "upstream" end will be used interchangeably and designate only the direction of travel or migration of analyte ions through the separation capillary 4, electrically-conductive junction 20, and flow detector mechanism 21 (to be described). As such, "input" or "upstream" specify the origin point from which analyte ions begin migration during separation, but need not specify the direction of electroosmotic or hydrostatic flow that occurs in any of the component elements comprising system 2 Further, the terms "downstream", "outlet" or "output" end may also be used interchangeably to designate the destination end (for analyte molecules) of the components used in the present invention.

As shown in FIG. 1, an electrode 14 coupled to a first voltage source 16 causes electrolyte solution 8 to be at a first electrical potential V1, typically in the range of about 5 kV to about 40 kV. A second voltage source 17 is coupled via electrode 18 to cause electrolyte solution 12 to be at a second electrical potential V2. Voltage source 17 preferably is also coupled via electrode 15 to cause solution 13 in intermediate container 9 to also be at the second potential V2. Preferably, electrolyte solutions 8, 12 and 13 are identical chemically, and potential V2 preferably is ground potential, e.g., 0 VDC.

Voltage sources 16 and 17 cause an incremental axial voltage drop along the separation path defined by capillary 4 and the upstream region of the electrically-conductive junction 20 (to be described). Depending upon the charged nature of the wall of separation capillary 4 and the polarities of voltage sources 16 and 17, the electroosmotic flow of electrolyte may be in the direction indicated by arrow A or by arrow B.

Capillary 4 has a mean inner diameter in the range of 5 $\mu$m to 500 $\mu$m, with 50 $\mu$m to 100 $\mu$m preferred, and a length of 5 to 150 cm, with 20 cm to 75 cm preferred, although other sized capillaries may be used. Capillary 4 is preferably made from a non-conductive material whose walls are a non-permeable material, silica for example. However, capillary 4 can be a fused silica capillary derivatized with an electrically-charged chemical functionality such as a silane reagent containing a carboxylate, sulfonic acid, phosphate, amino, quaternary amino or other electrically-charged moiety.

Alternatively, separation capillary 4 may be a fused silica capillary with inner walls coated with a polymer that contains the aforementioned charged or chargeable moieties. Furthermore, separation capillary 4 can be composed of a glass, such as borosilicate or alumino-silicate glasses, that can establish a charge layer at the inner wall.

In addition, separation capillary 4 might be a polymeric capillary such as Teflon®, polystyrene, polyethylene, etc., onto which a charge can be induced by physical adsorption of electrically charged molecules such as sodium dodecylsulfate, cetyltrimethylammonium bromide, polyethylenimine, etc. Separation capillary 4 may instead be composed of a neutral polymer (such as one of those listed above), to which a charge is imparted by chemical derivatization, such as sulfonation with sulfuric acid, sulfur trioxide, etc. The exact chemical composition or nature of the separation capillary is relatively unimportant, so long as the capillary possesses charged moieties on its surface or surface moieties that can be made to have a charge under some set of conditions.

Electrolyte solutions 8, 12 and 13 are buffers whose pH may be altered to promote anion or cation separation, although it is not required that electrolyte solutions 12 and 13 be the same as electrolyte solution 8. Electrolyte solutions 8, 12, 13 may be made from any number of common inorganic or organic salts, acids, and/or bases, such as sodium phosphate, citric acid, tris-hydroxymethylaminomethane (Tris), etc., whose solution pH may be altered to promote anion or cation separations. Of course, other electrolyte solutions known to those skilled in the art of capillary electrophoresis could be used instead.

An analyte detector mechanism 30 or 30A may be positioned at some point along capillary 4 (e.g., mechanism 30) or downstream from capillary 4 (e.g., mechanism 30A). In either case, mechanism 30 and/or 30A detects the separation of analyte ions of interest within the separation capillary during the separation process.

As noted, electrolyte solutions 12 and 13 are preferably both at potential V2, ground potential in the preferred embodiment. Thus, the downstream end of electrically-conductive junction 20 and all points downstream thereof to and including electrolyte solution 12 are at a common electrical potential V2.

A flow detection mechanism 21 (to be described) is disposed to monitor electroosmotic flow rate through the separation capillary 4. A signal indicative of the magnitude of electroosmotic flow through separation capillary 4 is transmitted from flow detection mechanism 21 via electrical leads 23 to a signal processing unit 27. Signal processing unit 27 transforms the electroosmotic flow rate input signal to a control signal on lead 29 that is preferably feedback-coupled to a control mechanism 33 (to be described). Control mechanism 33 can be operated to alter or otherwise control the magnitude of electroosmotic flow through separation capillary 4.

According to the present invention, electrically-conductive junction 20 serves to terminate the electrical field gradient or potential drop across separation capillary 4. This termination occurs by conducting the current resulting from the electrical field or potential drop established along separation capillary 4 through the wall of electrically-conductive junction 20 and to voltage source V2. Electrically-conductive junction 20 also provides a fluid coupling conduit between separation capillary 4 and flow detection mechanism 21, such that electrolyte solution within separation capillary 4 can freely travel to or from flow detection mechanism 21. In one embodiment of the present invention, electrically-conductive junction 20 also serves as an ion-exchange material, selectively passing a specific type of ion (e.g., cation or anion) through the wall of electrically-conductive junction 20.

The flow detection mechanism 21 preferably monitors some property of the fluid transported to or from the separation capillary 4 as a result of electroosmotic flow through capillary 4. Directly (or in conjunction with suitable electronics in signal processing unit 27), detection mechanism 21 provides a signal indicative of the magnitude of electroosmotic flow through separation capillary 4.

As noted, signal processing unit 27 outputs a control signal on lead 29 to permit control or alteration of electroosmotic flow in separation capillary 4 via on-line or manual feedback, shown generally as 38. Control of electroosmotic flow using a control mechanism 33 may be implemented in several ways. For example, a radial electrical field may be applied across the wall of separation capillary 4 using an externally-coated electrode as described by U.S. Pat. No. 5,092,972 to Ghowsi, and also U.S. Pat. No. 5,151,164 to Blanchard et al., and U.S. Pat. No. 5,180,475 to Young et al. These references disclose methods and mechanisms for intentionally varying the zeta potential within a separation capillary to influence electroosmotic flow rate therethrough. Alternatively, control mechanism 33 may include a variable pressure source to control pressure across the separation capillary 4, and thus vary the net fluid flow by augmenting or countering the electroosmotic flow with a hydrostatic flow component; see, for example, Baechmann et al., Git Fach2. Lab 37(6) (1993) 514–522.

Figure 2:
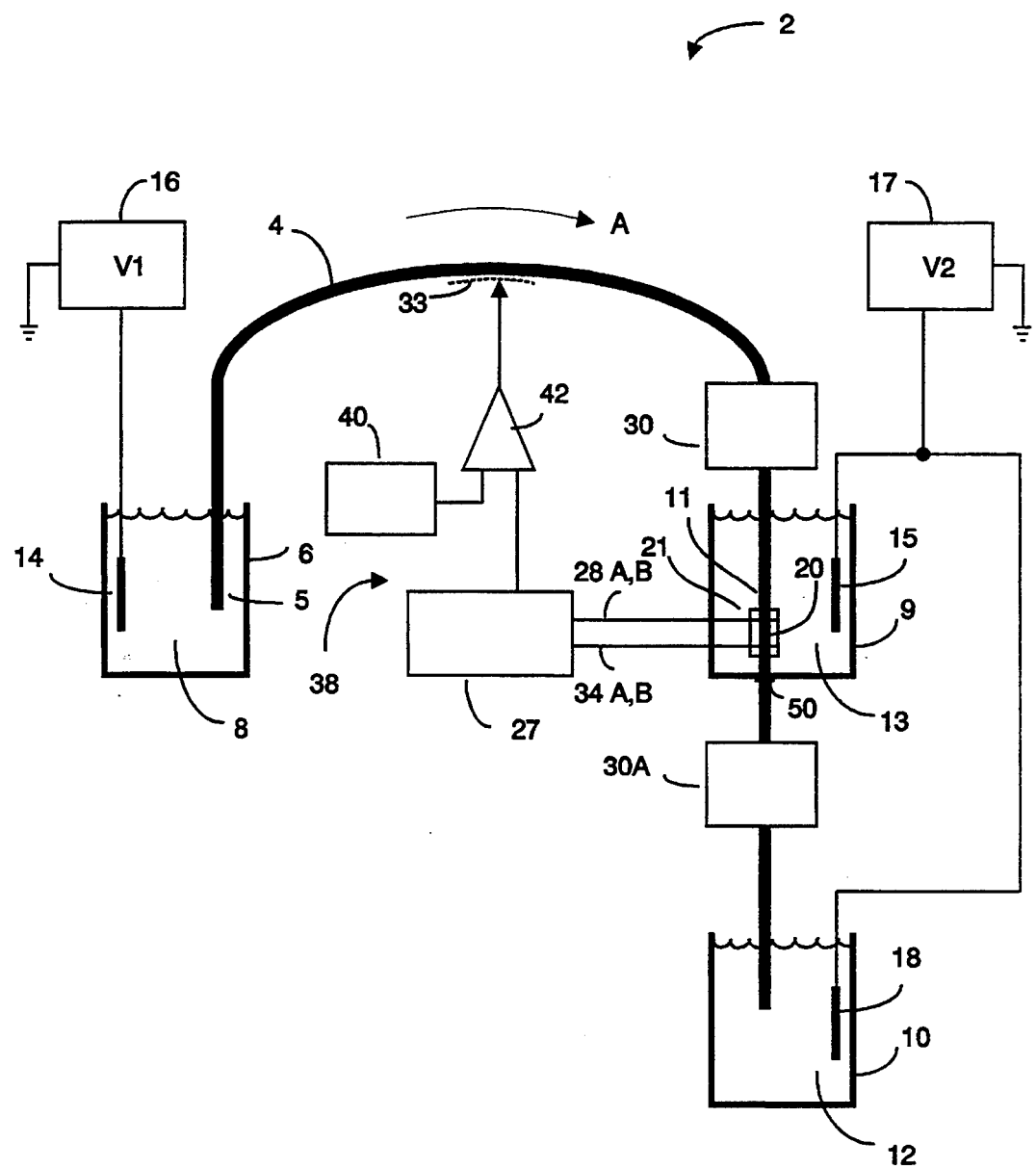
FIG. 2 depicts an embodiment of the present invention wherein the electrically-conductive junction is an ion-exchange membrane unit, and further depicts generic feedback control of electroosmotic flow using real-time monitoring data.

FIG. 2 depicts an embodiment of the present invention wherein the electrically-conductive junction 20 is an ion-exchange membrane unit that is used to establish a concentration difference between the upstream and downstream segments of the flow channel. In this embodiment, the concentration difference data provide a real time measure of electroosmotic flow rate, which measure may be used to control, e.g., using feedback mechanism 38, the electroosmotic flow rate through the separation capillary 4.

In FIG. 2, voltage source 16 again causes an incremental axial voltage along the separation path defined by capillary 4 and the upstream region of an electrically-conductive junction 20, an ion exchange membrane unit. A resultant electric field across the separation capillary 4 is produced that causes an axial electroosmotic flow from container 6 toward container 10, as depicted by the arrow A. The velocity of the electrolyte solution 8 as it moves electroosmotically in the capillary is proportional to $E \cdot \mu_{eo}$, where E is the electric field strength and $\mu_{eo}$ is the mobility of the bulk electrolyte.

According to this embodiment of the present invention, the bulk electrolyte flow is caused to pass through a channel that is defined, at least in part, by an ion-exchange membrane unit, shown generally as 20, which also constitutes the electrically-conductive junction. Ion-exchange unit 20 is coupled in series with the separation capillary 4, and unit 20's exterior membrane surface (see FIG. 3) preferably is in fluid communication with electrolyte solution 13 in container 9. Preferably unit 20's membrane surfaces are highly conductive such that the voltage V2 of solution 13 (preferably 0 VDC) establishes a like potential within the ion-exchange membrane unit channel.

Figure 3:
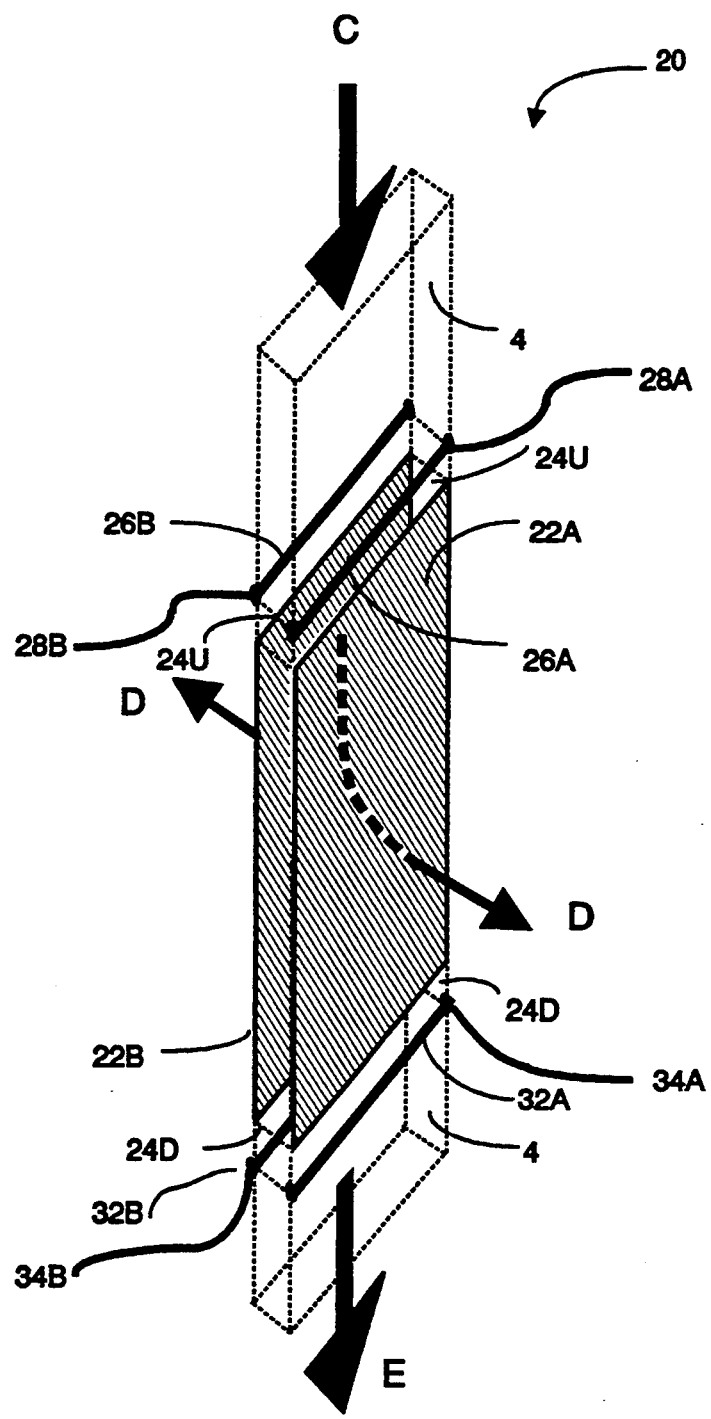
FIG. 3 is a detailed perspective figure of the ion-exchange membrane unit 20 depicted in the embodiment of FIG. 2.

FIG. 3 depicts ion-exchange membrane unit 20 in greater detail. For ease of illustration, ion-exchange unit 20 is depicted as including spaced-apart membranes 22A, 22B, separated from capillary 4 by upstream and downstream insulating gaps or spacers 24U, 24D. Membranes 22A and 22B in ion-exchange unit 20 partition electrolyte 8 solution flow and electrolyte 13 such that a chosen ion type within solution 8, e.g., anion or cation, is preferentially exchanged through the membranes into the surrounding electrolyte solution 13.

For example, if the analyte ion of interest is an anion, unit 20 will be a cation-exchanger. As such, cations in solution 8 flowing through unit 20 may pass through membranes 22A and 22B into solution 13, whereas anions in solution 8 within unit 20 remain in solution 8. Of course, if the analyte ions of interest were cations, unit 20 would be an anion-exchange membrane unit. The membrane surfaces of unit 20 may be made from, for example, Nafion TM material, available from E. I. DuPont de Nemours & Co. of Wilmington, Del., or from Permapure Corporation of Toms River, N.J. Unit 20 may take a variety of forms, including a short section of polymeric tubing with small internal diameter, typically 25 to 200 µm inner diameter, and preferably having the same inner diameter as the separation capillary 4. Ion-exchange unit 20 may in fact differ in appearance from what is depicted in FIG. 3. Unit 20 may be cylindrical, for example, wherein membranes 22A and 22B would be a single, continuous cylindrical membrane. In such embodiment, electrodes 26A, 26B preferably would be washer-like metallic disks placed upstream of unit 20. Similarly, electrodes 32A, 32B would be similar disks placed downstream of unit 20. These metallic washer-like disks preferably would be spaced apart from the membrane regions by washer-like insulator disks. (As such, the unit 20 configuration shown in FIG. 4 may be regarded as cylindrical.)

Adjacent the upstream gap 24U, spaced-apart electrodes 26A, 26B are coupled by electrical leads 28A, 28B to a mechanism 27. Similarly, adjacent the downstream gaps 24D, spaced-apart electrodes 32A, 32B are coupled by leads 34A, 34B to mechanism 27. In this embodiment, electrodes 26A, 26B, 32A, 32B are gold or stainless steel tips of conducting leads 28A, 28B, 34A, 34B, the tips being substantially flush with the inner capillary wall.

In this embodiment, mechanism 27 measures concentration of ions within the bulk electrolyte solution 8 upstream and downstream from ion-exchange membrane unit 20. Mechanism 27 may be any instrument producing a signal proportional to electrolyte solution concentration, e.g., a conductivity meter. Mechanism 27 may be an ultraviolet absorbance detector, provided that the electrolyte ions of interest absorb ultraviolet light and that electrodes 26A, 26B, 32A, 32B are replaced with suitable devices such as fiber optic cables, photo-emitter/photodetector, and the like. As such, mechanism 27 would measure the ultraviolet opacity of the electrolyte solution.

The electrolyte solution passing beyond the downstream region of unit 20 may be coupled to an analyte detecting mechanism 30A that signals the presence of analyte ions in the solution. However, preferably, analyte detection means is positioned upstream of the electrically-conductive junction 20 and flow detection means 21 as depicted by 30 in FIG. 2.

Detector 30, 30A may be a standard capillary electrophoresis detector, such as an ultraviolet photometer, a fluorescence detector, a conductivity meter, an amperometric detector, a potentiometric detector, or a suppressor followed by a conductivity detector. As all of these detectors are well known to those skilled in the art, they will not be described in detail herein.

According to the present invention, the upstream-to-downstream length of unit 20 is made sufficiently long to drop the potential gradient from voltage source 16 to voltage V2, at or before the downstream region of unit 20. So doing ensures that at least by the downstream region of unit 20, there will remain zero incremental axial voltage drop, and thus no axial field to produce an active electroosmotic driving force in any portion of the flow channel downstream of the downstream region of 20. Alternatively, an electrical lead from voltage source 17 could be coupled more directly to the downstream region of unit 20 to ensure that no incremental axial driving voltage remains, thereby eliminating the need for electrode 15. It will be appreciated from FIGS. 2 and 3 that because the surrounding electrolyte solution 13 is preferably at zero volts, the potential difference across or transverse to unit 20 will also be zero at the downstream region of unit 20.

Whereas analyte ions of interest are actively moved electroosmotically at positions upstream from unit 20, the elimination of an axial incremental voltage at least by the downstream region of unit 20 results in ions of interest having passive axial movement thereafter. In essence, these ions are swept along by the electroosmotic flow actively produced upstream, whereat an incremental axial voltage drop still exists.

In the series configuration shown in FIGS. 2 and 3, the flux of the electrolyte anions will be constant at any point along the series path, e.g., along capillary 4, through the upstream region, and through the downstream region of ion-exchange unit 20. This is a consequence of the ability of ion-exchange unit 20 to prevent the transport of ions from solution 13 into the flowing stream. Since anions are neither added to nor removed from the flowing stream, in this example, the flux of anions in the bulk electrolyte 8 upstream from unit 20 (e.g., upstream from means 26A, 26B) will therefore equal the flux of electrolyte anions at the downstream region of unit 20 (e.g., adjacent to means 32A, 32B).

In FIG. 3, arrow C denotes the bulk electrolyte solution and analyte anions and cations entering the upstream region of ion-exchange unit 20. Arrow D represent those electrolyte cations preferentially exchanged by unit 20. Arrow E, at the downstream region of unit 20, denotes the electrolyte solution and analyte anions and cations flowing out of the unit 20, enroute to analyte detector apparatus 30A.

Figure 4:
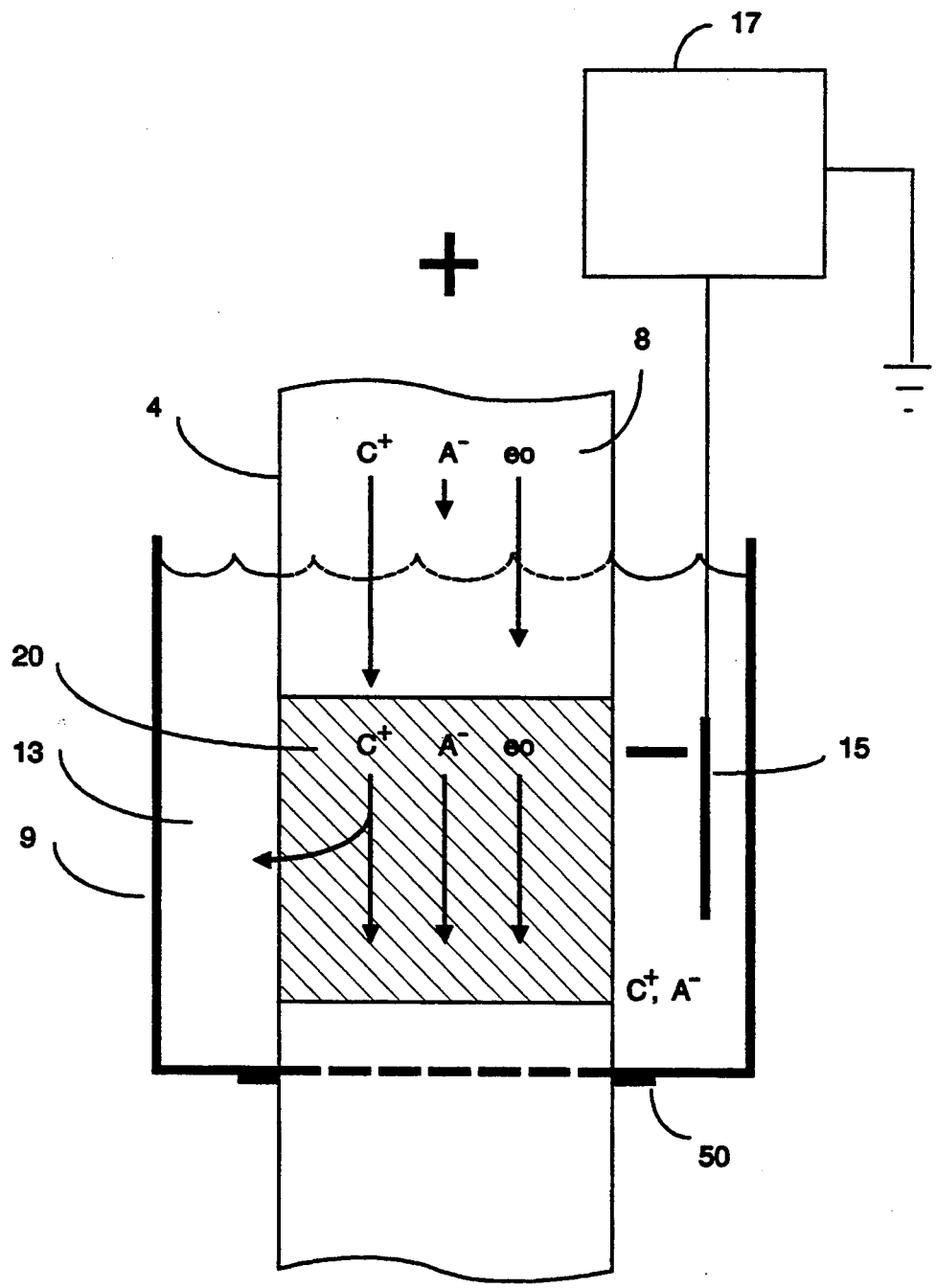
FIG. 4 is a schematic representation of net velocities of various electrolyte components within the ion-exchange membrane unit 20 of FIGS. 2 and 3.

FIG. 4 is a vector depiction of the ionic migration upstream and downstream from a cation-exchange membrane unit 20, according to the above-described embodiment of the present invention. In FIG. 4, in vector fashion the arrows depict the net velocity of cations (C+), of anions (A−), and of the electroosmotically moved bulk electrolyte solution (eo). The large plus and minus signs depict the polarity of the voltage gradient established by the voltage sources 16 and 17, shown in FIG. 2. In FIG. 4, solution 13 preferably is the same as solution 8, and, as noted, unit 20 may be considered to be cylindrical in cross-section, although it need not be cylindrical.

Upstream from unit 20, the electrolyte solution and ions therein are subject to electroosmotic forces due to an axial incremental voltage drop along the flow path. In FIG. 4, the positive voltage at the top of the path will repel cations in a downstream direction, and will attract anions in an upstream direction. Accordingly, cations will move downstream (e.g., toward the bottom of FIG. 4) with a greater velocity than anions. This velocity differential is depicted by the C+ vector length exceeding the anion A− vector length. In the FIG. 4 example, the eo vector length is shown intermediate in magnitude, indicating that electrolyte solution 8 flows downward with a net velocity exceeding that of anions but less than that of cations.

With further reference to FIG. 4, once the cation-exchange membrane unit 20 is encountered, some cations will be conducted out of unit 20 into solution 13, as evidenced by the curved C+ vector. Note, however, that within unit 20, at least in the downstream region whereat no incremental axial voltage from voltage sources 16, 17 remains, the net cation velocity has decreased, whereas the net anion velocity has increased. This result follows since there is no longer any positive charge from voltage source 16 to repel cations downward or to attract anions upward (in FIG. 4).

Thus, from and after the downstream region of unit 20, cations and anions are each swept passively further downstream by the electroosmotic flow from upstream. As shown in FIG. 4, after the downstream region of unit 20, cations and anions will have a net velocity equal to that of the flowing bulk electrolyte solution, namely the electroosmotic velocity. It will be appreciated that upstream as well as downstream the equivalents of anions must equal the equivalents of cations to maintain electrical neutrality. However since downstream there will be fewer cations than there were upstream (since unit 20 is presumed to be a cation-exchanger), there must be fewer anions downstream as well. Therefore the concentration of anions in the bulk electrolyte downstream will be less than the concentration upstream.

To recapitulate, within capillary 4 and the separation path at least until the upstream region of unit 20 is reached, electrolyte anion velocity v results from two transport phenomena: electroosmotic bulk movement of the overall electrolyte 8 and electrophoretic movement. This relationship is given by equation (1) as follows:

$$v(cm/sec) = (\mu_e + \mu_{eo}) \cdot E \quad (1)$$

where $\mu_e$ and $\mu_{eo}$ respectively denote electrolyte anion mobility and electroosmotic mobility of the source electrolyte solution 8, and where E is the field strength resulting from voltage sources 16, 17. It is understood that the quantities in equation (1) are vectors, each having magnitude and direction.

Thus, within capillary 4 and continuing to at least the upstream region of unit 20 adjacent to 26A and 26B, the electrolyte anion flux ($J_{A1}$) is given by:

$$J_{A1}\left(\frac{\text{moles}}{\text{sec} \cdot \text{cm}^2}\right) = C_1 \cdot v = C_1 \cdot (\mu_e + \mu_{eo}) \cdot E \quad (2)$$

where $C_1$ is the upstream anion concentration in the bulk electrolyte 8, measured in moles/cm$^3$.

Because unit 20 is at zero incremental voltage at least by the downstream region, the anion flux ($J_{A2}$) downstream from unit 20 is given by:

$$J_{A2} = \left(\frac{\text{moles}}{\text{sec} \cdot \text{cm}^2}\right) = C_2 \cdot \mu_{eo} \cdot E \quad (3)$$

where $C_2$ is the downstream anion concentration in the bulk electrolyte 8, measured in moles/cm$^3$.

But since anion flux in the upstream and downstream region must be equal, i.e., $J_{A1} = J_{A2}$, it follows that:

$$C_1 \cdot (\mu_e + \mu_{eo}) \cdot E = C_2 \cdot \mu_{eo} \cdot E \quad (4)$$

from which the following equation is obtained by algebraic manipulation:

$$\mu_{eo} = \frac{C_1}{C_2 - C_1} \cdot \mu_e = \frac{\mu_e}{\frac{C_2}{C_1} - 1} \quad (5)$$

Electrolyte solution conductivity ($\kappa$) is nearly proportional, but not quite directly, to bulk electrolyte concentration (C). Since the electrolyte anion mobility $\mu_e$ is known, an approximate value for the electroosmotic mobility $\mu_{eo}$ may be determined according to equation (5) from the measured conductivity ratio $\kappa_2/\kappa_1$. As a practical matter, the concentration $C_1$ may be measured anywhere upstream of unit 20. Further, since the concentration of the electrolyte solution 8 may be determined when the electrolyte solution is prepared, the upstream concentration $C_1$ need not be measured during actual operation. Thus, it will suffice for mechanism 27 to simply measure the downstream concentration $C_2$, which measurement is then compared to the known upstream concentration value $C_1$. If unit 20 is an anion-exchange junction, and $\mu_e$ represents the bulk electrolyte cation mobility, and $J_{A1}$ and $J_{A2}$ represent bulk electrolyte cation flux, then equations (1) through (5) are still applicable.

The use of an ion-impermeable conductive junction as a capillary electrophoresis ground electrode wherein the junction was fabricated from palladium metal has been reported by W. T. Kok and Y. Sahin, Anal. Chem. (1993) 65 2497-2501. Hydrogen gas is produced as a result of the reduction of water to hydroxide. Kok et al.'s use of palladium advantageously permitted the transport of hydrogen gas out of the flowing stream, since palladium is permeable to hydrogen but impermeable to liquids or dissolved ions. However, Kok et al. did not use their palladium metal electrode to determine electroosmotic flow or to alter or control electroosmotic flow.

In the case of an ion-impermeable conductive junction, this junction 20 will be electrically coupled to voltage source V2 in FIG. 2 (which is preferably at ground potential) and will normally replace electrode 15. (In this configuration, electrolyte 13 and container 9 are no longer needed and are not used.) Depending on the polarity of the high-voltage applied to the capillary, the ion-impermeable conductive junction 20 will serve as either the cathode and produce anions (e.g. as a result of the reduction of water to hydroxide) or serve as the anode and produce cations. In either case, these ions produced by electrolysis at the junction will be added to the bulk electrolyte solution.

In the case where the ion-impermeable conductive junction serves as the cathode and produces hydroxide, the flux of cations upstream from the junction will be equal to the flux downstream from the junction, since cations are neither removed from nor added to the bulk electrolyte solution at the junction. In addition, the equivalents of anions must equal the equivalents of cations to maintain electrical neutrality. Therefore, the change in bulk electrolyte concentration upstream and downstream from junction 20, which occurs in the case of an ion-exchange junction, will also occur in the case of the ion-impermeable conductive junction. As such, equations (1) to (5) remain applicable.

Consider the case where the bulk electrolyte solution is a buffer made from boric acid and sodium borate, and where the axial electric field is coupled to the capillary such that the ion-impermeable conductive junction serves as the cathode. In this configuration, the hydroxide produced at the junction will react with boric acid in the bulk electrolyte solution. This reaction will increase the concentration of borate anion in the downstream region of the ion-impermeable conductive junction. For this example to work, the flux of boric acid delivered to the junction must be equal to or greater than the flux of hydroxide produced at the junction.

In electroosmotic flow measurement applications, an ion-impermeable conductive junction may not be used where the junction will cause the electrolysis of both anions and cations. Consider, for example, the case where the bulk electrolyte solution contains a reducible cation, such as cupric ion. The cupric ion could be reduced to copper metal, and plate-out on the inner surface of the junction, as hydroxide was being produced by reduction of water.

Thus, according to the present invention, regardless of whether the conductive junction is an ion-exchange unit or an ion-impermeable unit, bulk electrolyte anions or bulk electrolyte cations must neither be added to nor removed from the electrolyte solution flowing past the conductive junction.

If $\mu_{eo}$ is observed to change during a run, as manifested by a real time change in $C_2/C_1$, the desired $\mu_{eo}$ value may be restored and maintained using a feedback mechanism 38 (see FIG. 2). Feedback mechanism 38 provides an output signal proportional to a desired rate of electroosmotic flow via a reference signal generator 40 and a comparator 42. Comparator 42 compares this reference level with an output signal from measuring device 27 that represents the actual electroosmotic flow condition. If there is a discrepancy between the desired and the actual rate of flow, an output signal from the comparator 42 is coupled to a mechanism for adjusting flow, shown generically as 33.

Figure 5:
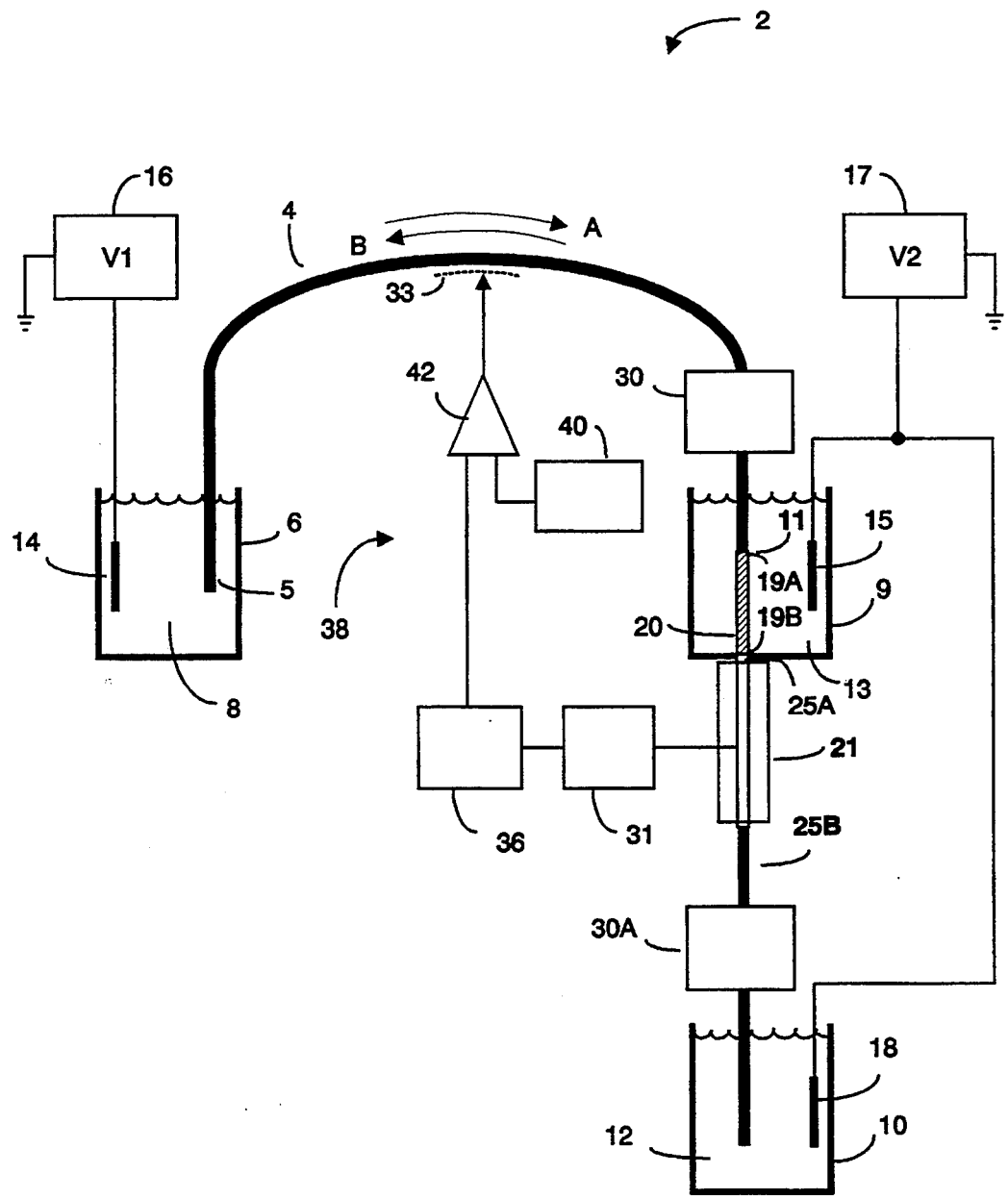
FIG. 5 depicts an embodiment of the present invention, wherein an electrically-conductive junction and a flow channel generate parabolic-flow related data in real time, and further depicting feedback control of flow using such data.
Figure 6:
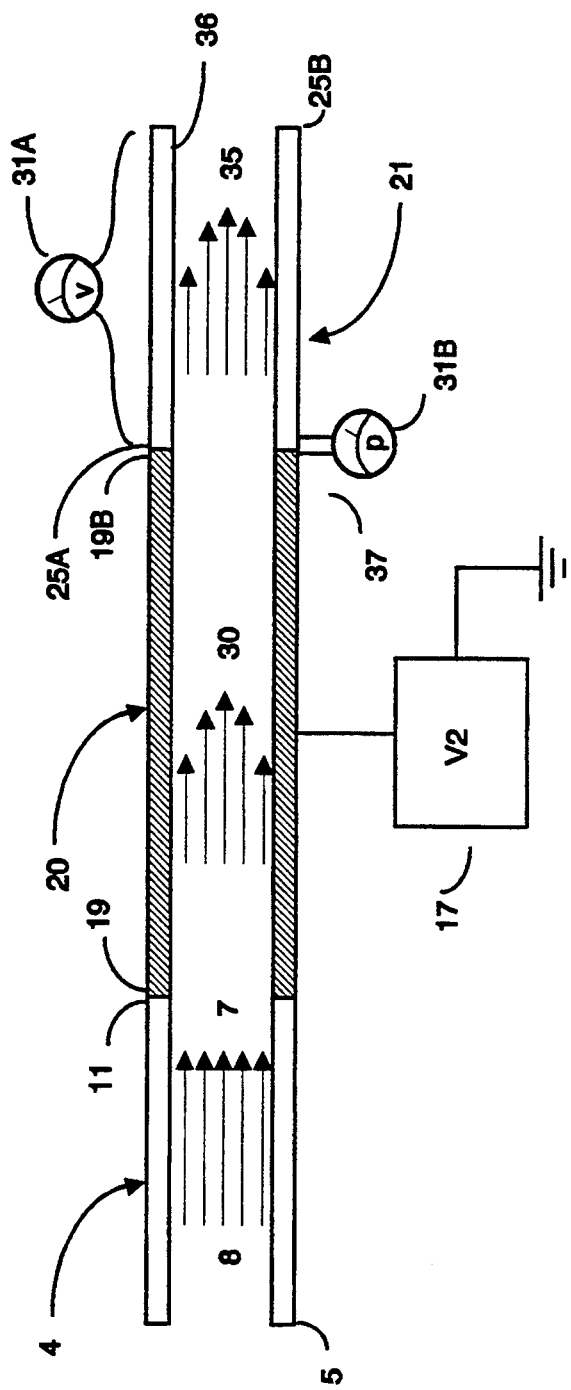
FIG. 6 depicts conversion of electroosmotic flow to parabolic flow within the electrically-conductive junction of FIG. 5.

FIGS. 5 and 6 depict a second and different embodiment of the present invention, wherein the electrically-conductive junction 20 transforms the electroosmotic plug-like flow from the separation capillary into a parabolic flow equivalent in magnitude to the electroosmotic flow. A parameter of this parabolic flow is measured to determine the electroosmotic flow in real-time.

FIG. 6 depicts the plug-like nature of the electroosmotic flow upstream from junction 20 by the uniform length velocity vectors 7 across the inner diameter of capillary 4. Similarly, the parabolic nature of the flow downstream from junction 20 is depicted by the staggered length velocity vectors 30 and 35. As will be described, measurement devices 31A and/or 31B preferably determine in real-time parabolic flow characteristics that relate directly to the electroosmotic flow rate through the separation capillary 4. As shown in FIG. 5, feedback mechanism 38, operating in response to such real-time data, may then adjust or otherwise control electroosmotic flow through the separation capillary.

In FIGS. 5 and 6, the electrically-conductive junction 20 terminates the voltage gradient generated from voltage sources 16 and 17, thereby transforming the original separation capillary electroosmotic flow into parabolic flow through flow detector mechanism 21. More specifically, as the electroosmotic plug-like flow enters the inlet 19 of the electrically-conductive junction 20, the incremental axial voltage gradient drops to zero along the electrically-conductive junction 20 and at all points downstream therefrom is zero. The result is conversion of the plug-like electroosmotic flow to the parabolic flow shown in FIG. 6. After transformation at junction 20, the resultant parabolic flow of fluid is "pushed" further downstream into detection mechanism 21.

Although FIG. 6 assumes electroosmotic flow follows the direction of arrow A in FIG. 5, it is understood that the reverse direction shown by arrow B could instead occur. In the latter case, electroosmotic flow originating in the separation capillary induces parabolic flow through the flow detection apparatus 21. This occurs because the electroosmotic fluid flow exiting separation capillary end 5 must "pull" a flow of electrolyte fluid 12 into flow detection mechanism 21 from reservoir 10. Again, since no voltage gradient exists in the detection mechanism 21 due to termination of the separation voltage gradient via electrically-conductive junction 20, the flow of fluid through 21 must be parabolic in nature.

In theory, electrically-conductive junction 20 could be an electrical conductor coupled to a constant voltage source such that zero incremental axial voltage exists everywhere along the junction length and at all points downstream. Absent an incremental axial voltage, electroosmotic flow can no longer exist, and the resultant flow is parabolic flow. Parabolic flow is characterized by an axial pressure differential across the conduit through which the parabolic flow occurs, as indicated by the staggered vectors 30, 35 in FIG. 6.

Those skilled in the art will recognize that electrolysis can generate gas bubbles within a metallic conductive junction coupled to voltage V2. In some cases, these bubbles could accumulate and undesirably alter the flow profile through the remainder of the system. To avoid this problem, junction 20 is preferably disposed away from voltage source 17 but in fluid and electrical communication therewith through a conductive electrolyte solution 13 that is at constant potential V2 via electrode 15.

Electrically-conductive junction 20 may be made from microporous material, for example, porous glass, porous ceramic, or porous polymer. Any electrolysis-generated gas bubbles would occur at the interface of solution 13 and electrode 15. As such, the bubbles would not affect the flow profile through the electrically-conductive junction 20 or the flow detection mechanism 21.

The electrically-conductive junction 20 may take many forms. Of course junction 20 must be electrically conductive to maintain current flow between the voltage sources 16 and 17, the latter preferably being at ground potential. Further, junction 20 should provide a restriction-free conduit for transport of the fluid flow from separation capillary 4 to the flow detection mechanism 21 (or vise versa if the direction of flow is in the opposite direction). Preferably the mean inner diameter of electrically-conductive junction 20 is in the range 5 $\mu$m to 500 $\mu$m, with 50 $\mu$m to 100 $\mu$m preferred, and the length of the junction 20 typically is in the range 50 $\mu$m to 5 cm, with 5 mm being suitable.

In the preferred embodiment, electrically-conductive junction 20 is a short section of porous glass capillary, available from Corning Glass, Corning, N.Y. Such material is described by Wallingford and Ewing (Analytical Chemistry (1987) 59 1762–1766). The porous glass capillary junction 20 has approximately 40 Å to 50 Å pores connecting the inner and outer wall surfaces. These pores are sufficient for electrical current conduction but are too small for free transport of fluid through the junction wall. Thus, current and selective ions can pass through the walls of the porous glass capillary 20 to terminate voltage V1. However, electrolyte fluid cannot easily pass through the small pores and the bulk fluid flow continues through the annulus of the porous glass capillary 20.

Alternatively, electrically-conductive junction 20 could be an electrically-conductive polymeric capillary tubing such as Nafion ® or sulfonated polystyrene. Nafion TM is available from Perma Pure, Inc., Toms River, N.J. Such polymeric material provides an electrically-conductive junction capillary 20 without pores, the electrical current passing through the capillary wall via an ion exchange mechanism. Electrically-conductive junction 20 could be fabricated from a porous polymer capillary such as used in dialysis or ultrafiltration devices. Porous polymers suitable for this application include (without limitation) polyacrylonitrile (available from Sepracor, Marlborough, Md.), polysulfone (available from A/G Technology, Dedham, Md.), and cellulose acetate.

The electrically-conductive junction 20 could be fabricated from a section of the fused silica separation capillary by laser-drilling a small (e.g., 25 $\mu$m to 100 $\mu$m) diameter hole in one wall of the silica capillary. The hole would be filled a sinterable glass or ceramic powder material, that is then fused. Such sinterable glass may be 1P 900 glass (available from Ferro Corp, Cleveland, Ohio), or ceramic to form a porous plug. Such a device is described in U.S. Pat. No. 4,908,116 to Zare et al.

Further, electrically-conductive junction 20 may be formed by fracturing a section near the end of the separation capillary 4. With the fractured ends in close proximity, the fracture is coated with a porous or conductive polymer solution that, upon evaporation of the solvent, casts a thin polymer film over the fracture. The polymer film will permit transport of current through the fracture and thus terminate voltage V1 from the separation capillary. However, the film is relatively impervious to bulk fluid flow and thus the electrolyte flow from the separation capillary will be transmitted through the electrically-conductive junction and be delivered to the flow channel of the flow detection mechanism. Whang and Chen in Analytical Chemistry (1992) 64 2461–2464 describe a porous polymer joint suitable for the electrically-conductive junction 20. Suitable conductive polymer joints are described by O'Shea et al. in J. Chromatography (1992) 593 305–312, and by U.S. Pat. No. 5,169,510 to Lunte et al.

Because the flow at the downstream end 19B of the electrically-conductive junction 20 is parabolic, the parabolic flowrate may be measured in many ways. As noted, separation capillary 4, electrically-conductive junction 20, and flow detection mechanism 21 are series-coupled. Thus, mechanism 21's measurement of parabolic flowrate can be directly related to the electroosmotic flow rate in the separation capillary 4.

Flow detection mechanism 21 includes a flow channel that is conducive to the formation of parabolic flow therethrough, and thus facilitates maintaining parabolic flow. Typically, such flow channel is a capillary conduit of similar cross-section and profile as that of separation capillary 4 and electrically-conductive junction 20. Thus, the flow channel may simply be a section of capillary, similar or identical in cross-sectional dimensions to the separation capillary. Alternatively, the flow conduit may be a channel machined through a solid block of material such as quartz, glass, plastic, etc, depending upon the property of parabolic flow that is to be measured.

Preferably, the output or downstream end 19B of electrically-conductive junction 20 is series-coupled with the input end 25A of the flow channel of the flow detection mechanism 21. As shown by the staggered velocity vectors 35 in FIG. 6, the flow through the flow detection mechanism 21 remains parabolic in profile. Where streaming potential or streaming current is to be measured, the flow detection mechanism is preferably made from a material that can maintain a high charge on the inner flow channel wall 36, for example, silica, glass, or charged polymeric material.

The flow channel of mechanism 21 can have a mean inner diameter in the range 5 $\mu$m to 500 $\mu$m, but preferably has a diameter equal to that of the electrically-conductive junction 20. So doing will enhance measurement sensitivity and preclude blockage of the flow of electrolyte through system 2. Mechanism 21's channel length may be about 10 cm or less. The flow channel mean inner diameter and length may be selected to enhance measurement sensitivity of the parabolic flow therethrough. However, excessive flow channel length can generate excessive back pressure in the separation capillary and degrade separations therein. (A typical length of the measurement capillary is 5 cm, but longer or shorter lengths can be employed depending upon the inner diameter of the measurement capillary 21.)

As shown in FIG. 5, the output or downstream end 25B of flow detection mechanism 21 can be coupled to an analyte detection mechanism 30A that signals the presence of analyte ions in the solution, as has already been described herein. Alternatively, the output 25B of mechanism 21 may be in direct contact with electrolyte solution 12 in fluid reservoir 10.

Flow detection mechanism 21 is actually an assembly which consists of a defined length of small internal diameter flow channel or conduit (typically but not necessarily a capillary) and a transducer which generates a signal related to the magnitude of the volumetric flow through the length of channel or conduit. In this discussion "capillary" is used to describe a small diameter flow channel; the "capillary" could assume the form of small diameter tubing such as that used for the separation capillary in the present invention, but the flow conduit in the detection mechanism 21 could also be formed by other means as will be described later. In a simple implementation of construction of the flow detection mechanism 21, two small holes are drilled into the wall of a section of fused silica capillary at some predetermined spacing distance and electrodes are inserted into these holes. The openings around the electrode wire are then sealed to make leaktight joints. The electrodes can be of some electrically conductive material, platinum or gold being a preferred material, but glassy carbon, graphite, stainless steel, aluminum, copper, nickel, silver, etc. also yield an acceptable electrode material.

In a slightly more complex implementation, the detection means consists of two short (e.g. 1 mm length) sections of conductive capillary material separated by a predetermined length of insulating capillary such as fused silica. A suitable conductive capillary material is stainless capillary hypodermic tubing available in 0.004 inch inner diameter from Small Parts, Inc., Miami Lakes, Fla. In this case, a conductive lead is soldered to each section of conductive capillary to facilitate connection to the device 27.

In another implementation, the flow conduit could be prepared by machining a channel of appropriate cross-section dimensions and length into a block of silica, glass, or charged polymer using conventional machine-shop technology; attachment of two conductive electrodes at a predetermined spacing along the flow conduit prepared in such a manner would complete the flow detection means assembly. Alternatively, the flow conduit could be prepared by photolithography or photoetching technologies such as those used to micromachine structures in silicon as described by Petersen, Proceedings of the IEEE (1982) 70 420–457.

In this preferred embodiment, the flow channel of detection mechanism 21 is made from a charge-retaining material, which material permits measurement of the streaming potential or streaming current generated by the parabolic flow through the flow channel of detection mechanism 21.

The magnitude of the streaming potential, which is measured with a millivoltmeter (or equivalent device), or streaming current, which is measured by a picoammeter (or equivalent device), may be in the mV or pA range, respectively. With reference to FIG. 5, device 31 measures differentially along an axial portion of the flow channel of mechanism 21, preferably from input end 25A to output end 25B. The magnitude of the measured potential or current will be influenced by the dimensions of the flow channel of detection mechanism 21. For example, a 20 $\mu$m length flow channel provides more signal than say a 5 $\mu$m length, and a 50 $\mu$m inner diameter capillary generates a larger signal than a 150 $\mu$m inner diameter capillary.

The magnitude of the streaming potential or current as read by means 31A is theoretically directly proportional to the parabolic flow rate through the flow detection means. This parabolic flow rate through the flow channel of detection mechanism 21 is volumetrically equivalent to the electroosmotic flow rate through the separation capillary. Thus, means 31A can provide a real-time signal proportional to the electroosmotic flow rate. Such signal may be used by a feedback system (to be described) to stabilize or otherwise control the electroosmotic flow rate. Those skilled in the art will appreciate that numerous instruments 31A can be used to provide such a signal in response to the differential streaming potential or streaming current. A suitable device for either of these measurements is a Keithley Model 614 electrometer (Keithley Instrument Co, Cleveland Ohio).

In a third and different preferred embodiment, the pressure differential associated with the parabolic flow rate through the flow channel of flow detection mechanism 21 is determined. As shown in FIG. 5, pressure meter 31B (or the equivalent) provides a signal which is a measure of the electroosmotic flow rate through the separation capillary. Those skilled in the art will recognize that the pressure at the interface of the electrically-conductive junction output 19B and flow channel input 25A (the "interface pressure") will differ from the pressure at the separation capillary input 5, or at the flow detection means output 25B.

More specifically, if separation capillary 4 possesses electroosmotic flow in the direction of electrically-conductive junction 20 and flow detection mechanism 21 (as depicted by Arrow A in FIG. 5), then the interface pressure will be greater than the ambient atmospheric pressure at the inlet and outlet ends 5 and 25B. In contrast, if separation capillary 4 is characterized by electroosmotic flow away from electrically-conductive junction 20 and flow detection mechanism 21 (as depicted by arrow B in FIG. 5), then the interface pressure will be lower than the ambient atmospheric pressure. In this embodiment, since streaming potential or streaming current is not measured, the flow channel of flow detection mechanism 21 need not be made from a charge-retaining material.

In this third embodiment, the property of the flow of fluid through flow detection mechanism 21 that is measured is the pressure drop generated across the flow channel of mechanism 21 due to parabolic flow of electrolyte fluid therein. Pressure measuring device 31B quantifies the pressure differential relative to atmospheric pressure associated with the parabolic flow, which measurement relates directly to the rate of electroosmotic flow thorough the separation capillary.

Those skilled in the art will appreciate that device 31B need not be a pressure meter per se. Device 31B could be a semiconductor-based pressure transducer, mounted in or incorporated as part of the flow channel of flow detection mechanism 21. The flow channel of flow detection mechanism 21 might also consist of a length of capillary to which is attached a pressure transducer at the upstream end of the capillary by laser-drilling a small hole in the side of the capillary wall.

Numerous pressure transducers are suitable for this purpose, such as Honeywell 142PC01D pressure sensor which produces a 0 to 8 volt signal for 0 to 1 PSIG or Honeywell 142PC05G, which produces a 0 to 8 V signal for 0 to 5 PSIG. Other suitable transducers would include Omega Model PX136-001GV, PX136-005GV, PX170-28GV among a number of devices available from Omega Engineering, Stamford Conn. A transducer such as Model EPI-050 or EPI-060 from Entran Devices, Fairfield, N.J., with active surface areas of about 0.01 cm$^2$ is particularly suited to this application. Another device suited to this application is described by Samaun et al. (I.E.E.E. Transactions on Biomedical Engineering, Vol. BME-20, No.2 (1973) 101–109), which consists of a low-volume piezoresistive pressure sensor device.

Ideally, the transducer used here should have small contact volume to reduce the response lag-time due to compressibility of the fluid in contact with the transducer element after a change in the pressure. Where separation capillary input 5 and output 25B are each at about one atmosphere (e.g., 14.7 PSIG), the interface pressure will be increased by about 0.9 PSIG for a flow rate of 0.6 μL/min as depicted by arrow A in FIG. 5, and a flow channel length 10 cm and mean diameter 50 μm. For the same flow rate, the interface pressure increase will only be about $5.9 \times 10^{-3}$ PSIG, when the flow channel has a length of 1 cm and a mean diameter of 100 μm.

The previous two embodiments of this invention are based on measurement of a characteristic of the parabolic flow of electrolyte fluid through a detection means. Those skilled in the art will also appreciate that other measurements may be made on the parabolic flow to determine the electroosmotic flow rate in the separation capillary.

Of course, electroosmotic flow rate may also be monitored and/or measured by introducing a tracer, e.g. a gas bubble, a thermal pulse, etc. at the one end of the flow channel of detection mechanism 21 and determining transit time through a predefined distance in the flow channel. The time required for the tracer to traverse to the opposite end of the flow channel will provide a measure of the electroosmotic rate of flow. This technique, however, has the disadvantage of requiring the introduction of a tracer into the flow stream, but may be practiced without converting the electroosmotic flow in the separation capillary to parabolic flow.

Returning now to FIG. 5, analyte detector 30 or 30A may be a standard capillary electrophoresis analyte detector, such as an ultraviolet photometer, an amperometer, a conductivity meter, a mass spectrometer, or a suppressor followed by a conductivity detector. As all of these analyte detectors are well known to those skilled in the art, they will not be described in detail herein.

The preferred embodiment for the location of the analyte detector is as depicted by 30 in FIG. 5, as detection in this location obviates all of the difficulties from broadening of the analyte bands upon transport through electrically-conductive junction 20 and flow detection mechanism 21 prior to detection as would be the case in position 30A of FIG. 5.

As noted, flow detection mechanism 21 in conjunction with 31A, 31B provide for real-time monitoring of the rate of electroosmotic flow in the separation capillary 4. The ability to determine electroosmotic flow rate in realtime permits the use of a feedback loop 38 to control the flow rate, for example, to maintain constant migration time, as shown in FIG. 5.

Feedback loop 38 would typically include a signal feedback circuit 36 that has an input coupled to receive the signal from flow detection mechanism 21 through means 31. Circuit 36 then provides an output signal to a differential amplifier 42 that compares this dynamic electroosmotic flow rate signal to a reference signal provided by a reference source 40. Amplifier 42 then provides an output signal proportional to desired rate of electroosmotic flow. This output signal is coupled to means 33 as discussed above for altering electroosmotic flow rate through separation capillary 4.

Means 33 may include, for example, electrical components that impose a controlled radial field across separation capillary 4, to impress or modulate the zeta potential, thus altering the electroosmotic flow. U.S. Pat. No. 5,092,972 to Ghowsi, U.S. Pat. No. 5,151,164 to Blanchard et al., and U.S. Pat. No. 5,180,475 to Young et al. disclose methods and mechanisms for intentionally varying the zeta potential to influence electroosmotic flow rate. Alternatively, means 33 may include a variable pressure source to modulate pressure across separation capillary 4, and thus vary the net fluid flow by augmenting or countering the electroosmotic flow with a hydrostatic flow component. Means 33 is known in the relevant art and will not be further described.

Figure 7:
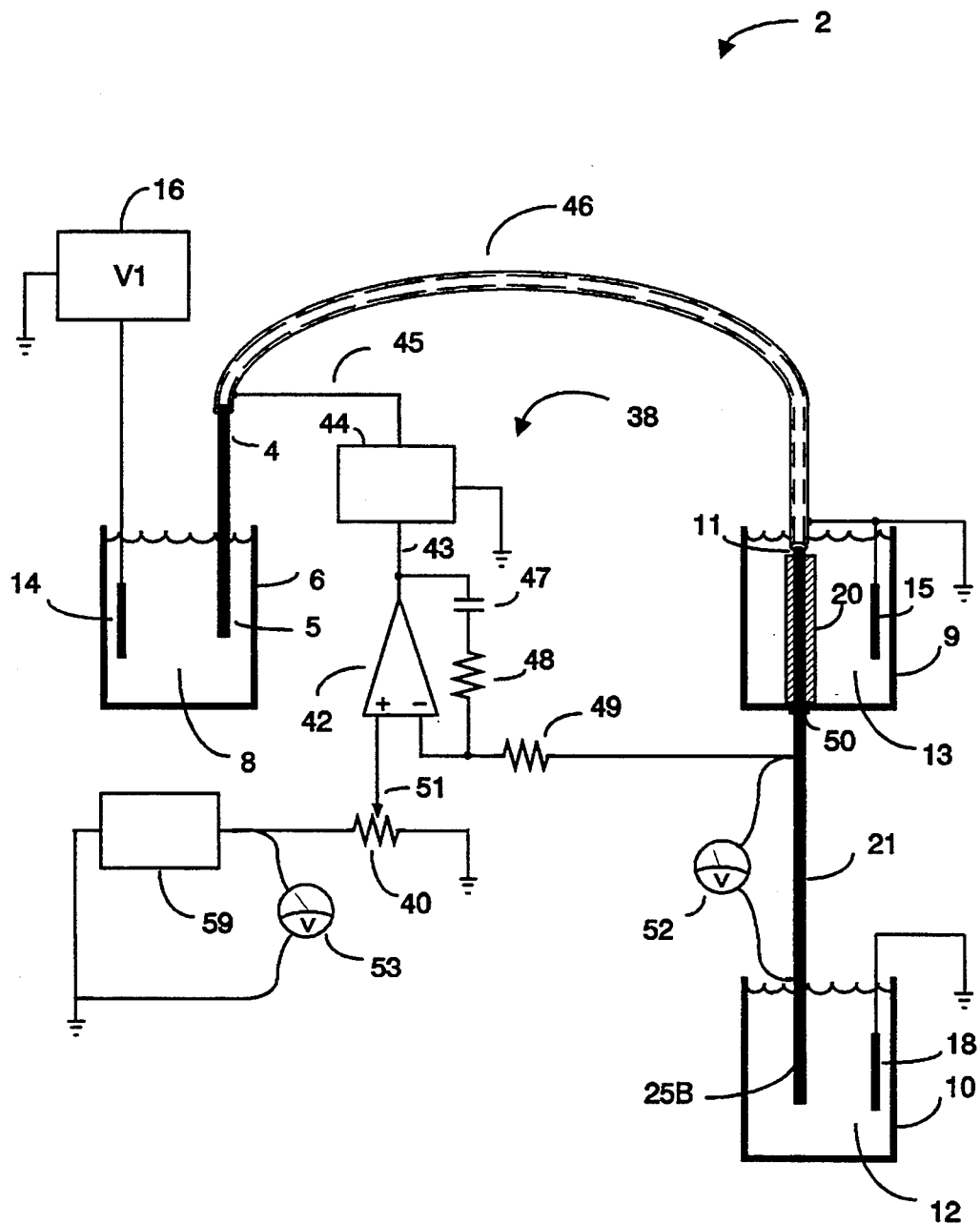
FIG. 7 depicts a feedback control mechanism used to maintain electroosmotic flow at a constant level, according to the present invention.

FIG. 7 illustrates a specific implementation of the present invention for on-line monitoring and real-time feedback control of electroosmotic flow such that the magnitude of electroosmotic flow will remain constant. A separation capillary 4 is series coupled to an electrically-conductive junction 20, which in turn is seriescoupled to a flow detection mechanism 21. The upstream end of the separation capillary 5 and the downstream end of the flow detection mechanism 25B are immersed in electrolyte solutions 8 and 12, respectively, held in containers 6 and 10. Also immersed in electrolyte solutions 8 and 12 are electrodes 14 and 18, which in turn are coupled to potentials V1 and V2, the latter preferably being ground potential. The electrically conductive junction 20 is also immersed in electrolyte solution 13 within container 9, which solution is preferably coupled to ground via electrode 15, ground potential being potential V2 referred to in earlier embodiments above.

As shown in FIG. 7, the output from flow detection mechanism 21 is coupled to the inverting input of an operational amplifier 42, coupled with capacitor 47 and resistor 48 to provide infinite DC gain. A reference signal (element 40 in FIG. 2) is provided by a variable resistor 40 coupled to a power supply 59, typically +10 VDC. The operational amplifier output is coupled on lead 43 to the typically 0–10 V voltage control of a conventional high voltage power supply 44. In response to the 0–10 VDC control signal on lead 43, power supply 44 provides an output that can vary from about 0 to 30 kV. Such controllable power supplies are known in the art, of which the Glassman Model MG30N100 (available from Glassman High Voltage, Whitehorse Station, N.J.) is typical.

The controlled power supply 44 high voltage output is coupled via high voltage cable 45 to one end of a high-resistance electrode 46, which sheath-like covers the exterior of separation capillary 4. The opposite end of high-resistance electrode 46 is coupled to ground. High-resistance electrode 46 may be formed by a number of methods, e.g., by coating the exterior of the capillary with a thin-layer of resistive polymer (Nafion TM), using resistive paste to produce electrical resistors, or other resistive material. Numerous types of material useful for producing resistive electrode 46 are known in the art and will not be discussed in detail here.

During operation, a voltage gradient is established across separation capillary 4 by voltage source 16 at one end, and by the electrically-conductive junction 20, which is at ground potential via electrode 15. The voltage gradient establishes electroosmotic flow through separation capillary 4, which flow is converted to parabolic flow of electrolyte upon termination of the voltage gradient by electrically-conductive junction 20.

The resulting parabolic flow of electrolyte is carried into flow detection mechanism 21, which monitors a property of the parabolic fluid flow, generating a signal that is coupled to the inverting input of operational amplifier 42. The flow detection mechanism 21 output signal is preferably also input to a voltmeter 52 for visual display. After establishing a stable electroosmotic flowrate through separation capillary 4, as gauged by the stability of the signal displayed by 52, the reference signal to the non-inverting operational amplifier input is set equal to the magnitude of the signal displayed by 52. This may be accomplished by adjusting resistor 40 until the reference signal (as displayed on voltmeter 53) is identical in magnitude to the signal displayed on voltmeter 52. With the proper feedback reference signal thus initially established, high voltage source 44 is then activated.

In a fashion known to those skilled in the art of control system design, the high voltage source 44 output is regulated by the signal on lead 43 provided by the operational amplifier 42 in response to changes in flow through flow detection mechanism 21. The thus controlled supply 44 high voltage output induces changes in the zeta potential at the inner wall of separation capillary 4, via the radial electrical field generated by high voltage in conjunction with electrode 46. Thus, zeta potential changes reflect changes in the flow rate as measured by flow detection mechanism 21. The desired result is that the output signal of flow detection mechanism 21 is maintained constant and equal to the reference signal 51 as provided by resistor 40.

EXAMPLES OF THE INVENTION

Example 1

Example of the Streaming Potential Generated in a Hydrostatically-Pumped Flow Detection Assembly Example 1 illustrates the magnitude and behavior of the streaming potential that can be generated in a flow channel through which electrolyte solution is moved via hydrostatic pumping at flowrates typical of those generated by electroosmosis in capillary electrophoresis separations. This example demonstrates that a significantly measurable voltage can be generated in the flow channel of the detection mechanism, if the electrolyte solution flows therethrough under parabolic flow conditions. In this experiment, hydrostatic flow conditions and flow velocities are selected to generate parabolic flow to emulate the signal expected from one embodiment of the present invention.

A 5.2 cm long section of 50 $\mu$m inner diameter fused silica capillary (available from Polymicro Technologies, Phoenix, Ariz.) was used as the flow channel of the detection mechanism. Each end of the fused silica capillary was inserted into a 7 mm long section of 0.015 inch inner diameter silicone peristaltic pump tubing (part number 116-0536-040, from Elkay Products, Shrewsbury, Md.). A 2 cm length of 0.10 mm diameter platinum wire (available from Johnson Matthey, Seabrook, N.H.) was inserted across the inner diameter of the silicone peristaltic pump tubing by first inserting a $30\frac{1}{2}$ gauge hypodermic needle (available from Becton Dickinson, Rutherford, N.J.) radially through the tubing, and then inserting 1 cm of the platinum wire through the cannulae of the needle. The needle was then withdrawn from the tubing, leaving a section of the platinum wire spanning the diameter of the tubing.

The wire was secured in place by the walls of the silicone tubing, which closed around the wire upon removal of the needle. Each end of the fused silica capillary was then abutted to the platinum wire spanning the inner diameter of the section of tubing on the end of the fused silica capillary. This assembly was then affixed to a common microscope slide via UV-cure epoxy (Dymax Corporation, Torrington, Conn.) using a Z7050 A UV source (Loctite Corporation, Newington, Conn.). The epoxy fixed the fused silica ends relative to the two platinum electrodes and also sealed any minute holes around the needle puncture tracks through which fluid might leak in subsequent experiments.

Electrolyte fluid was delivered through the flow channel via a 25 cm section of 100 $\mu$m inner diameter fused silica capillary, one end of which was attached to one end of the inlet of the flow channel assembly above-described.

The remaining end was attached to a pressurized reservoir (Pressurizable Reservoir Chamber 37053, Dionex Corporation, Sunnyvale, Calif.). Helium gas was used to pressurize the reservoir chamber using a 0–30 PSIG gas regulator (Norgren JR07-100-RNKA), the pressure being measured with a standard Bourdon 0–10 PSIG pressure gauge.

The two platinum electrodes in the above-described flow detection means were coupled to a Keithley Model 614 electrometer (Keithley Instruments, Cleveland, Ohio) used in the voltmeter mode. The downstream electrode was coupled to the positive (red) electrometer lead, whereas the upstream electrode was coupled to the negative (black) electrometer lead. A shielded triax lead was employed to input the signal to the electrometer, and the third or shielded lead was connected to a Faraday cage constructed around the above-described flow detection means assembly using commercially-available aluminum foil (Reynolds Aluminum, Richmond Va.).

Flow of electrolyte solution through the assembly was affected by establishing a fixed pressure in the reservoir chamber, which caused electrolyte solution to flow through the channel of the flow detection assembly. The electrolyte solution in this example consisted of 0.5 mM sodium borate decahydrate, borax (available from Sigma Chemical Co., St. Louis, Mo.). The solution was prepared by dissolving 0.1907 grams of the salt in 1 liter of 18 MΩ-cm water and filtering through a 0.2 μm filtration membrane (available from Millipore Corporation, Bedford, Md.). Flow was delivered through the flow detection assembly at volumetric flow rates such that turbulent flow conditions would be avoided. In the experiment, the Reynold's numbers for the fastest flows of electrolyte fluid through the capillary were less than 1, which is significantly below the 2100 value typical for the onset of turbulent flow.

The streaming potential was recorded as a function of flow rate by establishing a specified pressure in the reservoir and recording the potential (mV) developed across the two platinum electrodes in the flow detection assembly after a stable reading was established. The flow rate through the flow detection assembly channel was then determined by attaching a calibrated length of 100 μm inner diameter fused silica capillary to silicone tubing on the outlet of the assembly. A bolus of air was then introduced into the upstream end of the calibrated capillary and its travel was stopwatch timed. Volumetric flow rate could then be calculated, given the inner diameter of the calibration capillary and the time necessary for the bolus to traverse a known distance.

Figure 8:
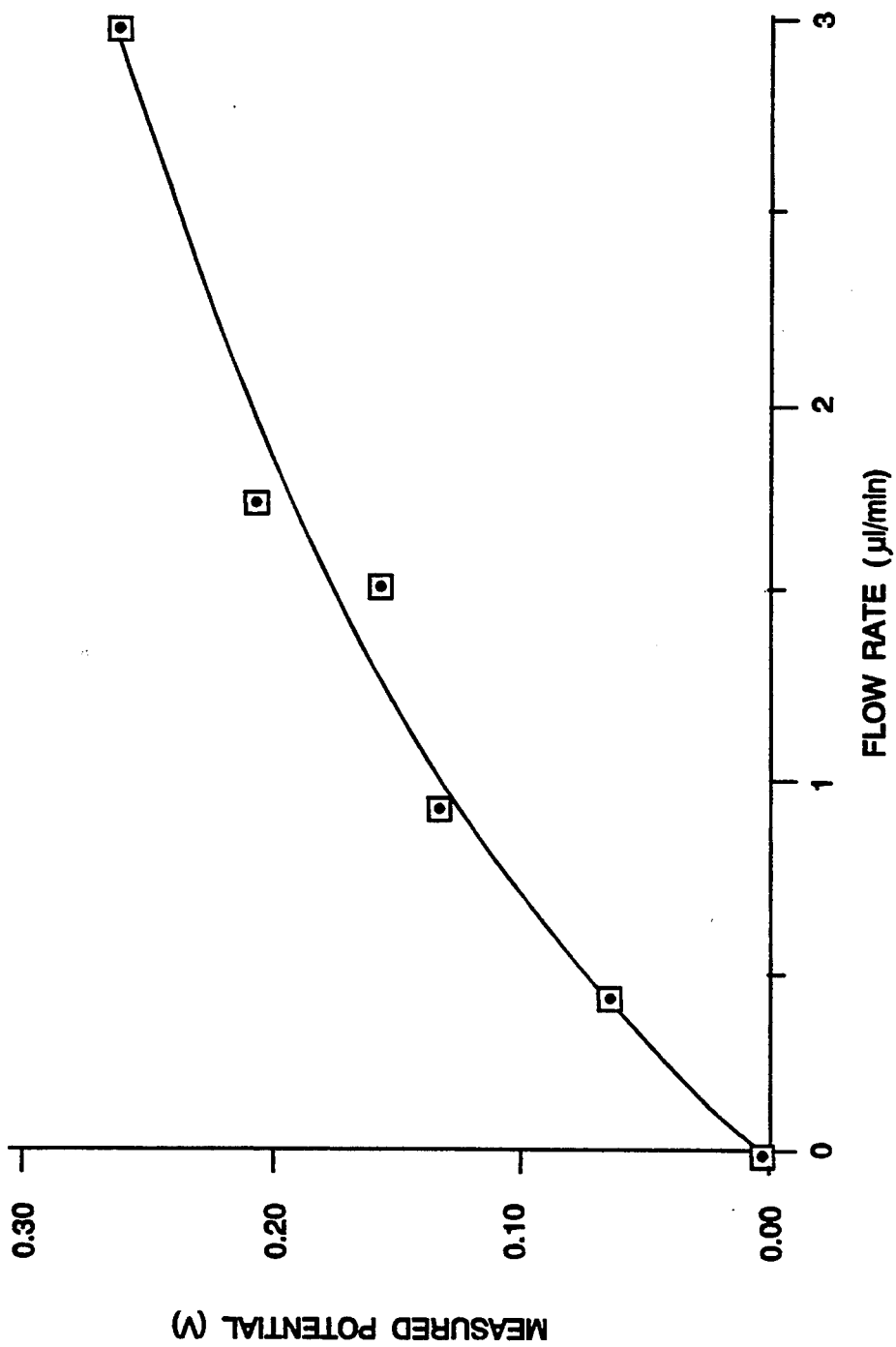
FIG. 8 is a plot of streaming potential data versus hydrostatic-pumped flow channel electrolyte flow rates, for the embodiment of FIG. 5.

FIG. 8 depicts measured streaming potential versus volumetric flow rate data acquired from this first experiment. As shown therein, streaming potential is a monotonic function of the parabolic flowrate of electrolyte fluid through the flow channel of the flow detection assembly. Streaming potentials in the several hundred millivolt range were obtained, signal magnitudes that are easily measured and processed using readily available electronic instrumentation.

Example 2

Example of the Streaming Potential Generated in a Hydrostatically-Pumped Flow Detection Assembly This example further illustrates the magnitude and stability of the streaming potential that can be generated in a flow detection assembly through which electrolyte solution is flowing via hydrostatic pumping. To implement this experiment, a 3 cm long section of 50 μm inner diameter fused silica capillary (Polymicro Technologies, Phoenix, Ariz.) was used. Each end of the fused silica capillary was inserted into a 7 mm long section of 0.015 inch inner diameter silicone peristaltic pump tubing (part number 116-0536-040, Elkay Products, Shrewsbury, Md.). A 2 cm length of 0.10 mm diameter platinum wire (Johnson Matthey, Seabrook, N.H.) was inserted across the inner diameter of the silicone peristaltic pump tubing by first inserting a 30½ gauge hypodermic needle (Becton Dickinson, Rutherford, N.J.) radially through the tubing and then inserting 1 cm of the platinum tubing through the cannulae of the needle. The needle was then withdrawn, the ends of the fused silica capillary were abutted to the platinum wire, and the assembly was affixed to a microscope slide in the same manner as described above with reference to Example 1.

Electrolyte fluid was delivered to the flow detection assembly from a reservoir (Pressurizable Reservoir Chamber 37053, available from Dionex Corporation, Sunnyvale, Calif.) through a 25 cm section of 100 μm inner diameter fused silica capillary. One end of this capillary was attached to one end of the flow detection assembly described above, and the other end was attached to the pressurized reservoir. Helium gas was used to pressurize the reservoir chamber using a 0-30 PSIG gas regulator (Norgren JR07-100-RNKA), the pressure being measured with a common Bourdon 0-10 PSIG gauge.

The two platinum electrodes in the above-described flow detection assembly were coupled to a Keithley Model 614 electrometer, as has been described with reference to Example 1. The 0-2 V isolated output of the Keithley electrometer was coupled to a laboratory strip-chart recorder that provided a permanent record of the streaming potentials derived in the experiment.

Flow of electrolyte solution through the assembly was affected by establishing a fixed pressure in the reservoir chamber, which caused electrolyte solution to flow through the flow channel of the flow detection assembly. The electrolyte solution in this example was identical to what has been described with reference to Example 1, as were non-turbulent flow conditions.

Figure 9:
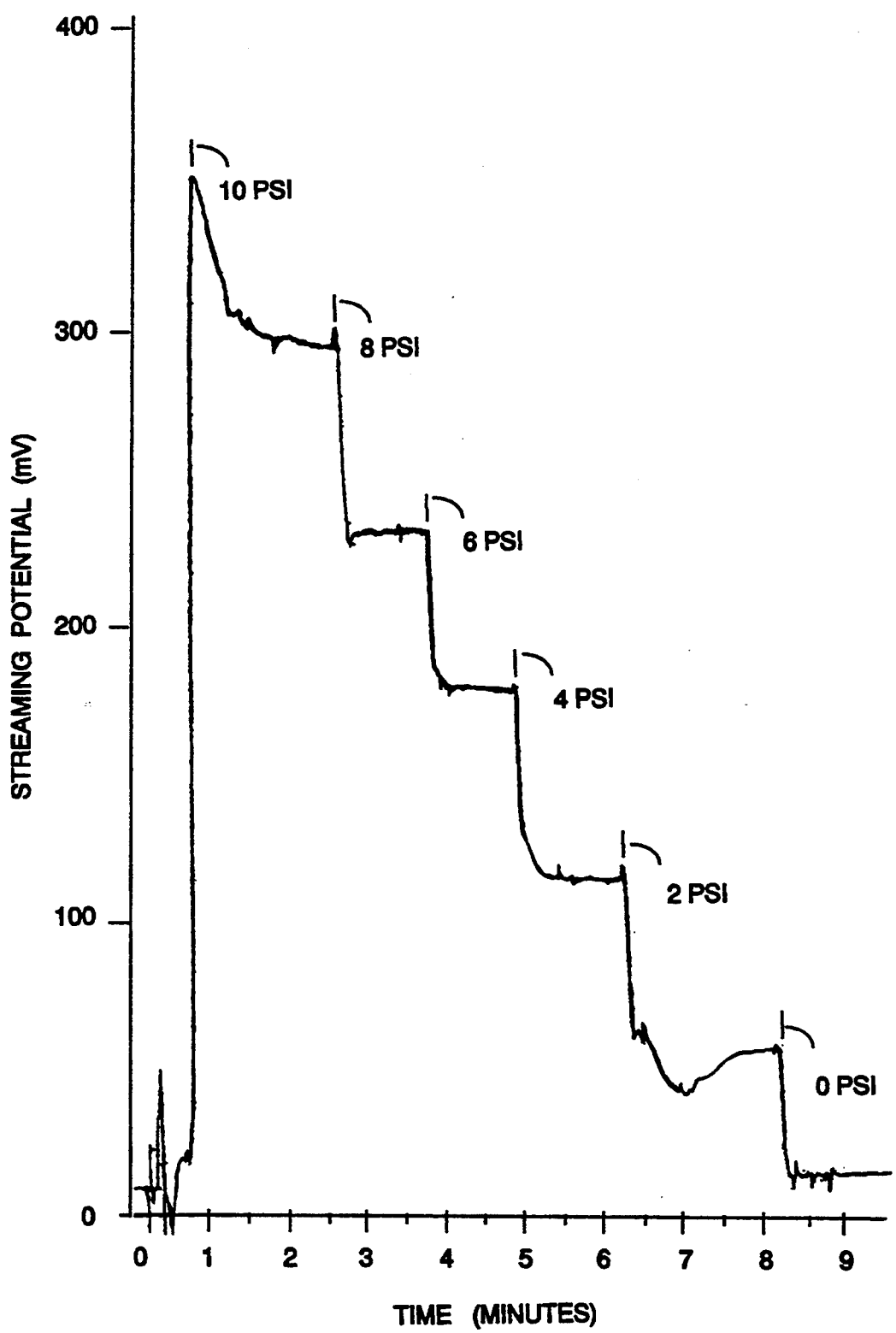
FIG. 9 is a stripchart recorder trace of measured streaming potential at various flow channel electrolyte flow rates for the embodiment of FIG. 5.

To implement this experiment, the electrolyte reservoir was pressurized to 10.0 PSIG with helium to establish stable flow of electrolyte through the flow detection assembly. The stripchart recorder was turned on at a 2.0 cm/min chart speed, with 500 mV full scale input range. After establishing a stable signal, the pressure in the electrolyte reservoir was sequentially reduced in 2 PSIG steps at approximately 1 minute intervals until 0 PSIG pressure was present in the reservoir. FIG. 9 shows changes in streaming potential occurring in the flow detection assembly, as recorded on the stripchart recorder.

According to theory, the streaming potential should be directly proportional to the volumetric parabolic flow rate through the flow detection assembly. Further, the magnitude of the laminar flow in the flow detection assembly flow channel should be directly proportional to the magnitude of the imposed pressure according to the Poiseuille equation. Thus, in this experiment, the magnitude of the measured streaming potential generated in the flow detection assembly should decrease monotonically with reduced pressure in the reservoir, e.g., with flow rate through the flow detection assembly.

FIG. 9 indeed demonstrates that measured streaming potential is a monotonic function of the parabolic flowrate of electrolyte fluid through the flow channel of the flow detection assembly. As noted, several hundred millivolt streaming potential signals are readily generated and measured.

Example 3

Example of Streaming Potential Signals Derived from Conversion of Electroosmotic Flow to Laminar Flow To implement this experiment, a 4.8 cm long section of 50 μm inner diameter fused silica capillary (Polymicro Technologies, Phoenix, Ariz.) was used to construct the flow detection assembly. Each end of the fused silica capillary was inserted into a 7 mm long section of 0.015" inner diameter silicone peristaltic pump tubing (part number 116-0536-040, Elkay Products, Shrewsbury, Md.). A 2 cm length of 0.10 mm diameter platinum wire (available from Johnson Matthey, Seabrook, N.H.) was inserted across the inner diameter of the silicone peristaltic pump tubing by first inserting a 30½ gauge hypodermic needle (available from Becton Dickinson, Rutherford, N.J.) radially through the tubing and then inserting 1 cm of the platinum wire through the cannulae of the needle, as has been described with reference to Experiment 1.

Into one section of the silicone tubing attached to the above-described flow detection assembly was inserted a 1.0 cm section of 100 μm inner diameter, 380 μm outer diameter porous glass capillary (available from Corning Glass, Corning N.Y.). The inserted end of the porous glass capillary was abutted to the platinum electrode spanning the inner diameter of the silicone tubing. To the free end of the porous glass capillary was then attached an 80 cm section of 100 μm inner diameter fused silica separation capillary (available from Polymicro Technologies, Phoenix, Ariz.) using a 7 mm length of 0.015" inner diameter silicone tubing, as described above.

At this point, a continuous flow channel assembly comprising a length of separation capillary, a short section of porous glass capillary, and finally a flow detection assembly is formed. The entire assembly was then stabilized using microscope slide and UV-cure epoxy, as was described with reference to Experiment 1.

A 2 cm length of 0.1 mm diameter platinum wire (Johnson Matthey, Seabrook, N.H.) grounding electrode was then attached to the microscope slide. One end of the platinum electrode was positioned in close proximity (<1 mm gap) to the porous glass capillary, and the other end of the platinum electrode was run out to the nearby edge of the microscope slide, where it was coupled via a test lead to ground. Contact between the porous glass capillary and the exposed end of the ground electrode was affected by applying several drops of the 0.5 mM borate electrolyte solution to cover both the porous glass capillary and the platinum electrode. The borate electrolyte immediately filled the pores of the porous glass capillary and established electrical communication between the earth ground electrode and the interior of the porous glass capillary. This configuration served to provide a ground for the high-voltage applied through the separation capillary, which voltage induced the electroosmotic flow through the capillary.

The two platinum electrodes in the above-described flow detection assembly were coupled to a Keithley Model 614 electrometer used in the voltmeter mode, whose output was coupled to a stripchart recorder, all as has been described above.

Electrolyte solution flow through the separation capillary/porous glass capillary/flow detection assembly was established by inducing electroosmotic flow in the separation capillary. The resultant flow would be the normal type of flow encountered in a typical capillary electrophoresis separation. The electrolyte solution in this example was 0.5 mM sodium borate decahydrate, borax (Sigma Chemical Co., St. Louis, Mo.), prepared by dissolving 0.1907 grams of the salt in 1 liter of 18 MΩ-cm water and filtering the resultant solution through a 0.2 μm filtration membrane (available from Millipore Corporation, Bedford, Md.). To deliver electrolyte flow through the above described assembly, the free end of the separation capillary was immersed in a 1 mL volume of this borate electrolyte solution. Also immersed in this 1 mL volume of electrolyte solution was a platinum electrode coupled to the positive terminal of a high voltage power supply unit of a capillary electrophoresis instrument (Model CES I, available from Dionex Corporation, Sunnyvale, Calif.).

To recapitulate, this experiment generated electroosmotic flow of electrolyte solution through a separation capillary by applying a high voltage to the capillary upstream end while the downstream end was grounded. The resultant electric field induced electroosmotic or plug flow through the separation capillary. The separation capillary is in direct fluid communication with the flow detection assembly via the porous glass capillary. Thus, the flow of fluid from the separation capillary can be quantitatively transferred via the electrically conductive junction through the flow channel of the flow detection assembly. However, as a intermediate step, the fluid flow is transformed from an electroosmotic plug-like flow profile in the separation capillary to a parabolic flow profile in the flow channel of the flow detection assembly. This transformation occurs in the porous glass capillary, which effectively grounds the electrical field required for inducing electroosmotic flow. As a consequence of parabolic flow, a streaming potential is developed in a manner directly analogous to that already demonstrated in Example 1.

To implement this experiment, the capillary electrophoresis system was programmed to initially impose 25 kV at the separation capillary inlet. At specified times thereafter, sequentially lower voltages were imposed at the separation capillary inlet, e.g., 22.5 kV, 20 kV, 17.5 kV, . . . 2.5 kV, 0 V.

Figure 10:
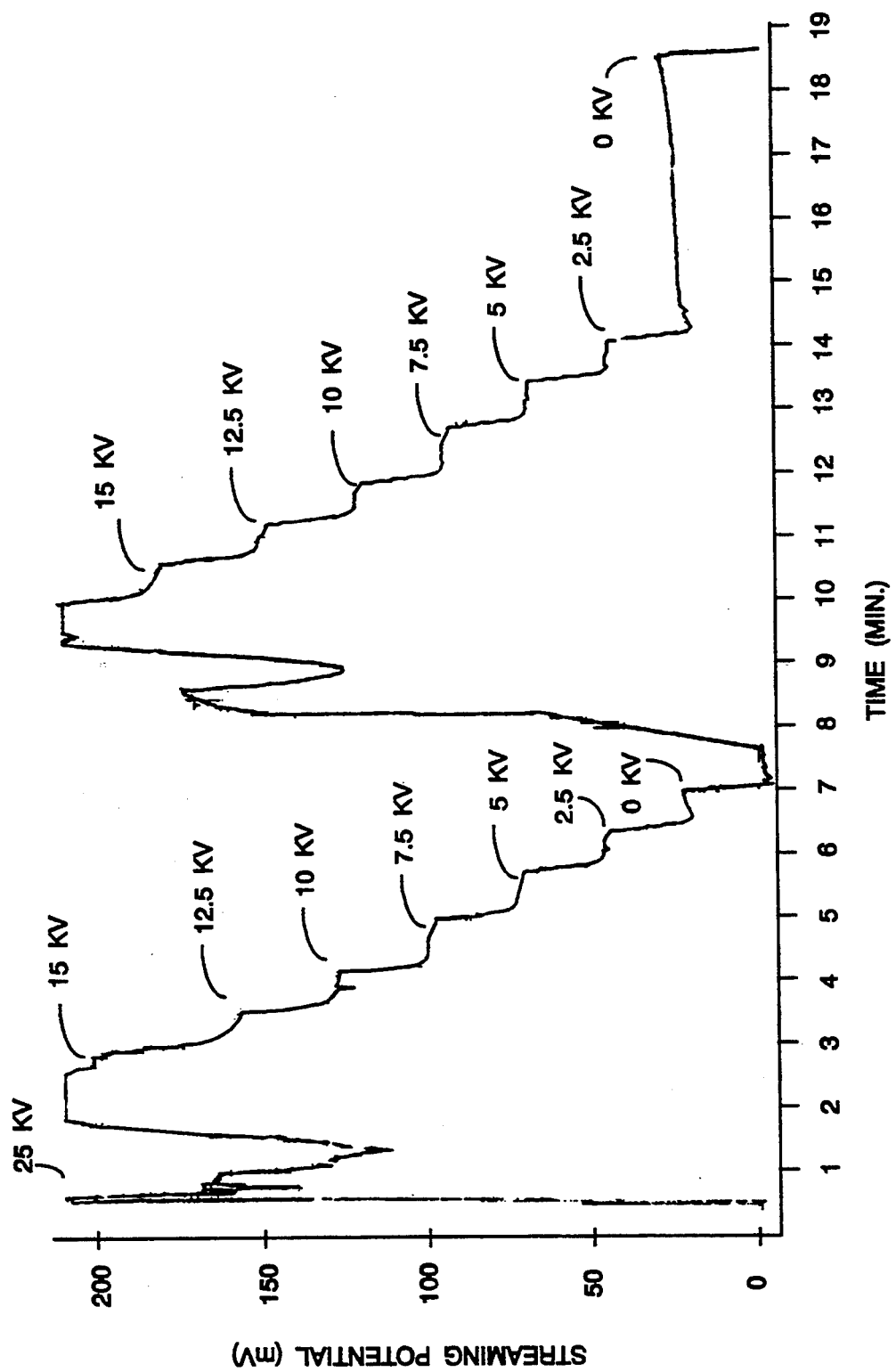
FIG. 10 is repetitive stripchart recorder traces of measured streaming potentials at various flow channel electrolyte flow rates for various applied high voltages, for the embodiment of FIG. 5.

FIG. 10 summarizes the data acquired in two sequential repetitions of this experiment. As shown therein, imposing 25 kV induced a large electroosmotic flow, and a relatively large streaming potential (>200 mV) in the flow detection assembly. As the magnitude of the imposed voltage was reduced, the magnitude of the electroosmotic flow through the separation capillary and thus the magnitude of the parabolic flow through the flow detection assembly was reduced. At 0 V applied separation voltage, no electroosmotic flow was induced in the separation capillary, no parabolic flow would exist in the flow detection assembly channel, and 0 mV streaming potential was observed. This agrees with theory, which predicts that the streaming potential should be directly proportional to the volumetric parabolic flow rate. Further, one would expect the magnitude of the electroosmotic flow in the separation capillary to be directly proportional to the magnitude of the imposed high voltage. FIG. 10 indeed confirms a monotonic decrease in the magnitude of the measured streaming potential generated in the flow detection assembly as the magnitude of the high voltage in the separation capillary is reduced.

Thus, the experiment of Example 3 illustrates the functionality of the present invention by demonstrating that an electroosmotic fluid flow can be converted into a parabolic fluid flow by grounding the electrophoresis-producing electric field. The experiment further demonstrates that useful magnitudes of monotonically-related streaming potential are readily generated under actual conditions encountered during actual electrophoresis capillary separation.

Example 4

Example of the Streaming Current Generated in a Flow Detection Assembly

This example illustrates the magnitude and stability of the streaming current that can be generated in a flow detection assembly through which electrolyte solution flows. A continuous flow channel, and ground electrode were constructed, each as described with reference to Example 3. Again, several drops of 0.5 mM borate electrolyte solution were used to cover the porous glass capillary and the platinum electrode, and the platinum electrodes were connected, as earlier described, to a Keithley Model 614 electrometer, which was now used in the ammeter mode. As before, a Faraday cage was constructed, and the 0–2 V isolated output of the Keithley electrometer was coupled to a laboratory stripchart recorder that recorded the streaming currents derived in this experiment.

Flow of electrolyte solution through the separation capillary was affected by establishing a fixed pressure in the reservoir chamber. The electrolyte solution in this example was as described with reference to Experiment 3, and again the flow was delivered under non-turbulent conditions.

The streaming current was recorded as a function of flow rate by establishing a specified pressure in the reservoir, and recording the pA streaming current developed Example 5

Figure 12:
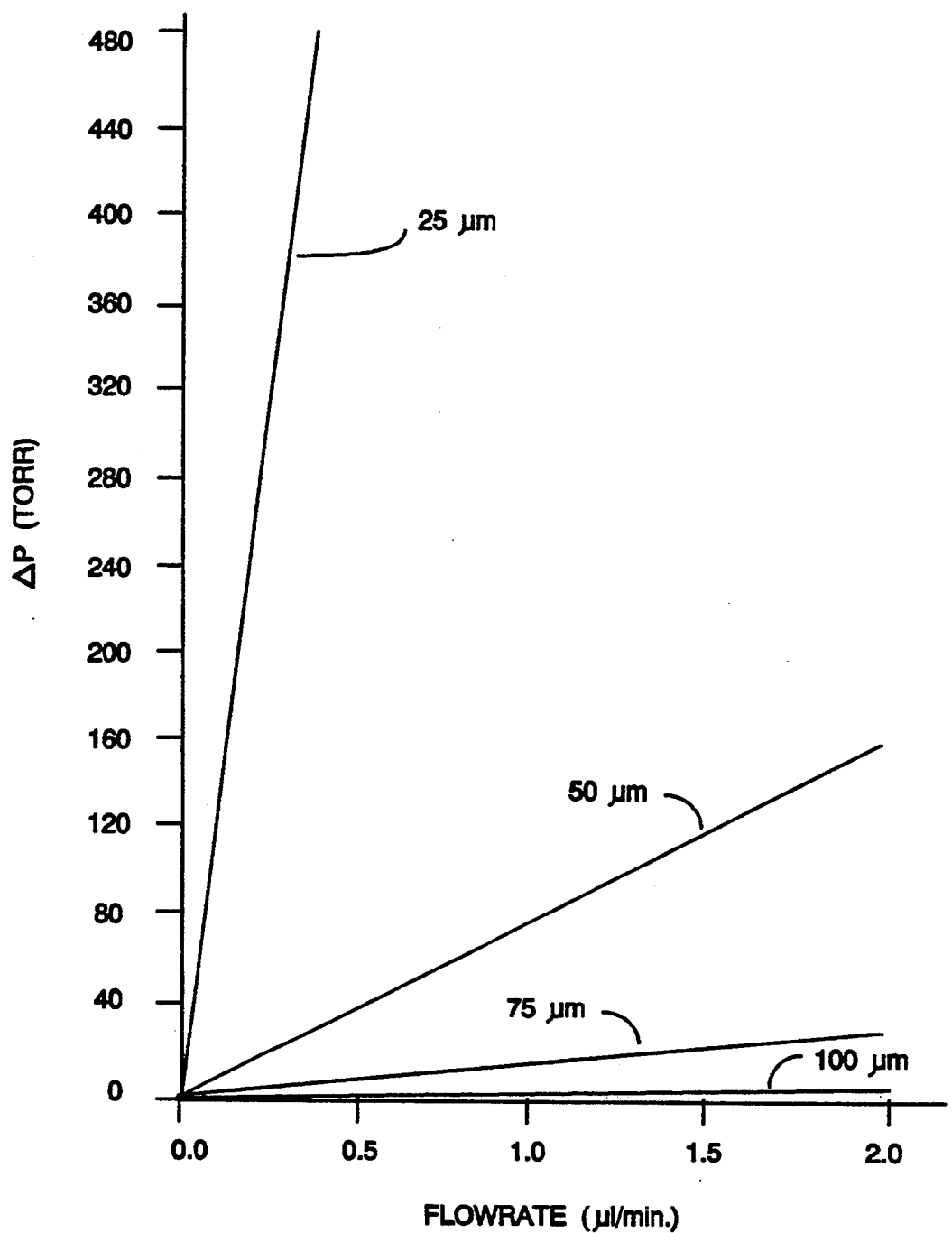
FIG. 12 is a plot of calculated pressure differential across fixed length flow channel having specified inner diameters, for the embodiment of FIG. 5.

Calculation of the Pressure Drop Generated In a Flow Detection Assembly at Various Laminar Flowrates This example demonstrates that readily measurable pressures can be generated in a flow channel of reasonable length. As shown by FIG. 12, a plot of the calculated pressure differential ($\Delta P$) between the inlet and outlet of measuring capillaries of various internal diameters varies linearly with flow rate. Calculations were performed using the Poiseuille equation, namely, $$\Delta P = \frac{8 \cdot \eta \cdot L \cdot F}{\pi \cdot r^4}$$

where $\eta$ is the electrolyte solution viscosity (0.01 Poise assumed for dilute aqueous solutions normally used in capillary electrophoresis), L is the length (cm) of the flow channel in the flow detection assembly, F is the volumetric flow rate (cm$^3$/sec) of electrolyte through the flow channel, $\pi$ is a constant, and r is the flow channel radius (cm). In FIG. 12, the flow channels were 10 cm in length.

The data shown in FIG. 12 were calculated from the above equation, converting the pressure to torr units. As shown, pressures of several hundred torr can easily be generated with 10 cm lengths of flow channel in the flow detection mechanism, and in fact, pressures as low as $1 \cdot 10^{-6}$ torr are measurable with commercially available laboratory instrumentation.

Example 6

Device for Determining the Pressure Drop Generated In a Flow Detection Assembly For Capillary Electrophoresis This example illustrates an embodiment of the present invention wherein the pressure drop generated in the flow detection assembly due to separation capillary electroosmotic flow is measured. A 27 cm length of 50 $\mu$m inner between the two platinum electrodes in the flow detection mechanism assembly once a stable reading was established. The flow rate through the flow detection assembly was then determined using a calibrated capillary length and a bolus of air, as described with reference to Example 1.

To implement this experiment, the electrolyte reservoir was pressurized to 10.0 PSIG with helium, to establish stable flow of electrolyte through the above-described assembly, as described with reference to Experiment 2. After establishing a stable signal, the reservoir pressure was sequentially reduced in 2 PSIG steps at approximately 1 minute intervals until 0 PSIG pressure was present in the reservoir. The pressure was then increased in approximately 2 PSI increments at one minute intervals until the 10 PSI level was reached. Flow detection assembly streaming currents in the 100 pA range were obtained and recorded on the stripchart recorder, operated at 2.0 cm/min, 1 V full scale.

Figure 11:
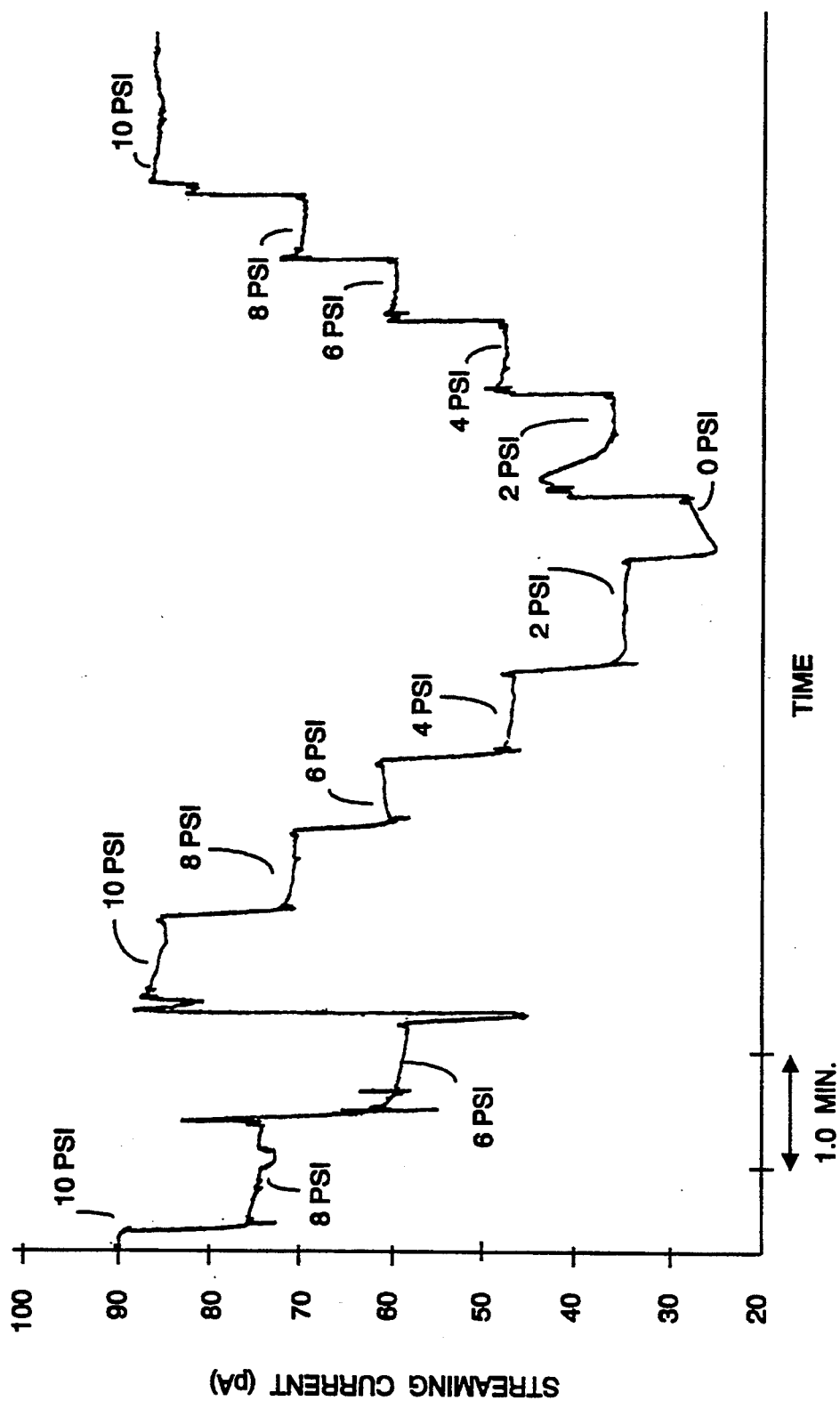
FIG. 11 s a stripchart recorder trace of measured streaming currents at various flow channel flow rates, for the embodiment of FIG. 5.

FIG. 11 depicts the stripchart record of the streaming current measured at different electrolyte reservoir pressures. The data depicted confirms what theory predicts: streaming current is directly proportional to the volumetric parabolic flow rate through the flow detection assembly flow channel, and further, parabolic flow rate in the flow channel is directly proportional to the magnitude of the imposed pressure, according to the Poiseuille equation. Thus, FIG. 11 depicts the expected monotonic decrease in the magnitude of the measured streaming current generated as the pressure in the reservoir (e.g., parabolic flow rate in the flow channel) is reduced. diameter 350 $\mu$m outer diameter fused silica capillary (available from Polymicro Technologies, Phoenix, Ariz.) was used as the flow channel of the flow detection assembly. This capillary was attached to two approximately 1 cm long sections of 100 $\mu$m inner diameter, 350 $\mu$m outer diameter fused silica capillaries by inserting all three sections of capillary into the three branches of a polypropylene Tee fitting (available from Cole Parmer Instrument Co, part # 6565), which was used as an alignment fixture. The ends of the three capillary sections were butted against one another to form a branched flow channel inside the alignment Tee. The three capillary sections were then fixed in place by cementing each to the alignment tee.

The approximately 1 cm length of capillary, which was coaxial with the flow channel of the flow detection mechanism, was then attached to a 7 mm length of porous glass capillary (available from Corning Glass, Corning N.Y.) using a 5 mm long section of 0.015" inner diameter silicone peristaltic pump tubing (available from Elkay Products, Shrewsbury, Md., part no. 116-0536-040). The free end of the porous glass capillary was then attached to a 100 cm section of 100 $\mu$m inner diameter fused silica separation capillary (available from Polymicro Technologies, Phoenix, Ariz.), using a 7 mm length of 0.015" inner diameter silicone tubing as described above.

At this point, a continuous flow channel consisting of a length of separation capillary, a short section of porous glass capillary, an intermediate short section of capillary, and finally a section of 50 $\mu$m inner diameter flow channel is formed, having a branch capillary at right angles. The branch capillary was then inserted into the inlet port of a pressure transducer (Honeywell Microswitch part no. 142PC05G) and the entire structure was then stabilized by attaching all capillary and connection components downstream of the separation capillary/porous glass capillary interface to a plastic box.

A grounding electrode made from a 2 cm length of 0.1 mm diameter platinum wire (available from Johnson Matthey, Seabrook, N.H.) was then immersed in small plastic reservoir filled with 2 mm borate buffer. One end of the platinum electrode was positioned in close proximity (<1 mm gap) to the porous glass capillary. The other electrode end was run out to the nearby edge of the microscope slide, where it was coupled to ground using a conventional electrical test lead.

Contact between the porous glass capillary and the exposed end of the ground electrode was affected as described with reference to Example 3.

The pressure transducer was powered by a 12 volt DC power supply (Lambda Electronics, Melville, N.Y., Model LUS-8A-12) operated from 120 VAC line voltage. The pressure transducer was operated as a current source by coupling a 10 KΩ resistor between the output and ground transducer terminals. The transducer output was coupled to a voltmeter (Fluke Series 12) and/or a stripchart recorder.

Flow of electrolyte solution through the entire flow assembly of separation capillary/porous glass capillary/flow detection assembly was established using electroosmotic flow from the separation capillary. The electrolyte solution in this example was 2.0 mM sodium borate decahydrate (borax), available from Sigma Chemical Co., St. Louis, Mo. The solution was prepared by dissolving 0.7927 grams of the salt in 1 liter of 18 MΩ-cm water, and filtering the resultant solution through a 0.2 μm filtration membrane (available from Millipore Corporation, Md.).

To deliver electrolyte flow through the above described assembly, the free end of the separation capillary was immersed in a 1 mL volume of the above-described borate electrolyte solution. Also immersed in this 1 mL volume of electrolyte solution was a platinum electrode coupled to the positive voltage high-voltage power supply unit of a capillary electrophoresis instrument (available from Dionex Corporation, Sunnyvale, Calif., Model CES I).

As in experiment 3, experiment 6 created plug-like electroosmotic flow of electrolyte solution through a separation capillary by applying a high voltage to the upstream separation capillary end, while the downstream separation capillary end was grounded. Here, grounding was achieved using a section of porous glass capillary bathed in electrolyte solution and coupled to ground potential. Because the separation capillary was in direct fluid communication with the flow detection apparatus, via the porous glass capillary, the fluid flow from the separation capillary was quantitatively transferred the flow detection assembly. However, as an intermediate step, the plug-like electroosmotic flow profile in the separation capillary was converted to a parabolic flow profile in the porous glass capillary, which effectively grounded the electrical field required to induce electroosmotic flow. As the resultant parabolic flow traversed the flow detection mechanism flow channel, a pressure drop results. The differential pressure drop can be quantified from the voltage output provided by a pressure transducer.

Figure 13:
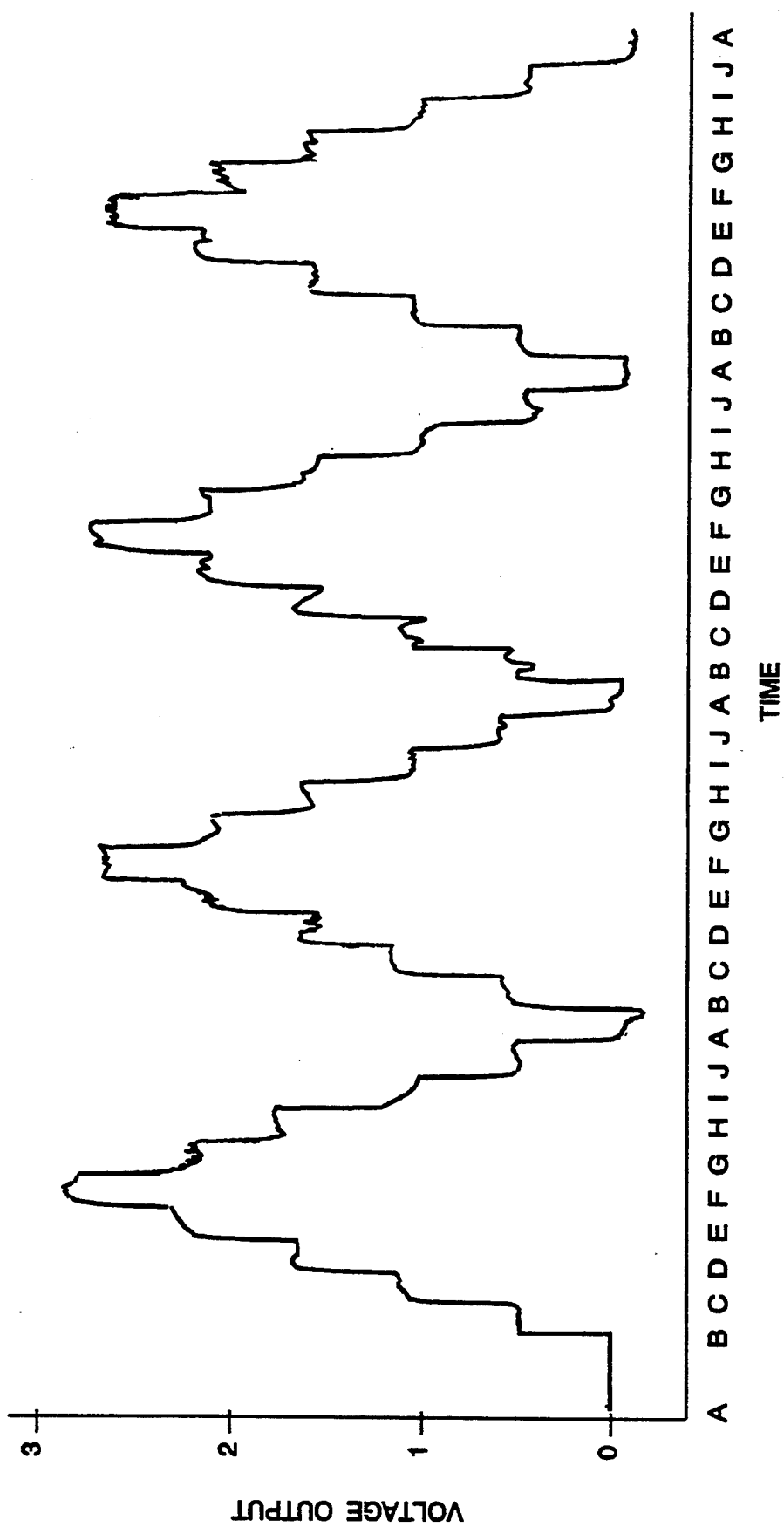
FIG. 13 is a stripchart recorder trace of repetitive experiments of the measured pressure differentials for various electrolyte fluid flow rates, for the embodiment of FIG. 5.

FIG. 13 depicts the results of four repetitive experiments, showing pressure transducer voltage output as a function of time. During the experiment, various flow detection assembly flow channel pressure drops were generated by inducing electroosmotic flows of various magnitudes in the separation capillary. The various electroosmotic flows resulted from imposing various electrical fields across the separation capillary at times denoted by the letters along the horizontal time axis of FIG. 13. As seen from FIG. 13, parabolic electrolyte flow through the flow detection mechanism generates a measurable pressure drop, using flow detection mechanism capillary dimensions typical of dimensions used to affect separations in capillary electrophoresis.

In FIG. 13, the stripchart recorder was set at 10 V full scale to record the 0 V to 5 V pressure transducer output over the course of the experiments. At time point A, 0 kV was applied across the separation capillary. Not surprisingly, since 0 kV does not induce electroosmotic capillary flow, essentially zero voltage output from the pressure transducer results. At times B,C,D,E, and F, the electrical field impressed across the separation capillary was increased sequentially in 5 kV steps and held for a duration before the next step increment, until a 25 kV field was impressed at time F.

Because the electroosmotic flow magnitude through the separation capillary should be directly proportional the magnitude of the imposed electrical field, the pressure drop across the flow detection assembly channel should increase monotonically and stepwise as the separation voltage is increased. This expected result is borne out by the data shown in FIG. 13. At time G in the experiments, the separation voltage was then decreased in 5 kV steps until 0 kV was imposed across the separation capillary. This process was then repeated 3 times to demonstrate the reproducibility of the measurement process.

Example 7

Generation of a Signal Related to Electroosmotic Flow Via Measurement of Concentration Differential The test apparatus included a section of polyimide-clad fused silica capillary (75 μm inner diameter, 60 cm length, obtained from Polymicro Technologies, Phoenix, Ariz.) connected to a cation-exchange membrane tube. The membrane tube was made from sulfonated styrene-grafted Teflon TM tubing, approximately 75 μm inner diameter, 3 mm long, and was immersed in a destination vial of electrolyte solution. A 12 kV potential was applied between the source and destination vials. The source vial, separation capillary, and destination vials were each filled with the same electrolyte, 2 mM borax or 5 mM taurine.

In this experiment, changing electroosmotic flow was simulated by applying supplemental pressure to the source vial to speed-up the flow rate. Electrolyte conductivity upstream from the cation-exchange tube was determined in a separate measurement rather than using conductivity electrodes placed immediately before the ion-exchange tube. An electrode for measuring electrolyte conductivity downstream from the cation-exchange tube was placed at the tube exit and a second conductivity detector electrode (which also served as the high-voltage ground) was placed in the electrolyte in the destination vial. Temperature in the apparatus was controlled at 26° C., but the separation capillary was not actively cooled.

The data in TABLE 1, below, lists ratios of electrolyte concentration upstream (e.g., before entering the cation-exchange tube) $C_1$, and downstream (e.g., after exiting the tube) $C_2$. Concentrations were calculated from a standard calibration curve of conductivity versus concentration. Column three in TABLE I lists measured values of velocity, v, divided by electric field strength, E.

This quantity represents electroosmotic mobility when no supplemental pressure is used. However, as noted, supplemental pressure was used to simulate changing electroosmotic mobility.

Equation 5 herein was used to calculate concentration values $C_2/C_1$ in column 5 of TABLE I, using the known values of simulated electroosmotic mobilities from column three and the known electrolyte anion mobilities.

TABLE 1

| Electrolyte | Supp'l. Pressure (psi) | v/E cm²/V·sec | C₂/C₁ Measured | C₂/C₁ Calculated |
| --- | --- | --- | --- | --- |
| 2 mM Borax | 0 | 0.00100 | 0.6 | 0.64 |
| | 0.2 | 0.00123 | 0.71 | 0.71 |
| | 0.5 | 0.00158 | 0.77 | 0.77 |
| | 1.0 | 0.00214 | 0.84 | 0.83 |
| 5 mM Taurine, | 0 | 0.00095 | 0.66 | 0.62 |
| 3 mM NAOH | 0.25 | 0.00126 | 0.74 | 0.71 |
| | 0.5 | 0.00153 | 0.80 | 0.77 |
| | 1.0 | 0.00209 | 0.85 | 0.83 |

The above data indicate agreement between the measured and calculated concentrations of electrolyte anions in the stream effluent from the ion-exchange membrane. The conductivity signal in this case being the signal related to the electroosmotic flow through the system.

Example 8

Device and Circuitry for On-Line Monitoring and Control of Electroosmotic Flow

This example illustrates monitoring and controlling electroosmotic flow through an electrophoresis separation capillary using the monitoring components described in Example 4, and using feedback control circuitry to maintain electroosmotic flow at a constant preset value. In this example, and as shown in FIG. 7, the output of the Keithley Model 614 electrometer is coupled to the inverting input of the operational amplifier (a Texas Instruments model TLC2201), configured as described in Example 7. Reference signal 51 is derived by dropping the output of a Model LUS-8A-12 power supply (available from Lambda Electronics, Melville, N.Y.) to ground through a 10 KΩ variable resistor. Values of resistors 48, 49 and capacitor 47 are empirically determined during testing of the feedback control circuitry. High voltage module 44 is a Model EL40R01 supply, available from Glass High Voltage.

In example 8, the external electrode is prepared by coating an approximately 10 μm thick layer of resistive ink on the exterior of the capillary using an air brush sprayer unit. The resistance of the external electrode is about 1 GΩ, as determined by the Keithley electrometer operated in the ohmmeter mode. Voltmeters 52 and 53 are Fluke Series 12 multimeters (available from Fluke Instrument Company, Everett, Wash.).

Electroosmotic flow through the separation capillary is established by imposing high voltage from a Glassman Model E140R01 power supply to the source vial 6, as depicted in FIG. 7. Once the flow through the system achieves a stable level (as gauged by the stability of the signal from voltmeter 52), a reference signal is established by adjusting resistor 40 such that the magnitude of signal on meter 53 is identical to that on meter 52. High voltage source 44 is then activated.

Flow stability is determined by the stability of the signal derived from meter 52 during the course of running. Electrolyte flow through the system is artificially altered by applying back-pressure to vial 10, which has the effect of opposing the electroosmotic flow through the separation capillary. Again, stability of the electroosmotic flow is gauged by the stability of the output signal on voltmeter 52. Further, flow stability is also gauged by gravimetrically determining the mass of electrolyte pumped per unit time from the source reservoir 6 to the destination reservoir 10 under different conditions.

In summary, the above eight examples demonstrate four different embodiments of the flow detection mechanism, and two different embodiments of the electrically-conductive junction, according to the present invention. Further, a specific embodiment for flow control feedback system 38 for on-line control of electroosmotic flow is described.

Modifications and variations may be made to the disclosed embodiments without departing from the subject and spirit of the invention as defined by the following claims.

What is claimed is:

1. A real-time method for determining electroosmotic flow rate during separation by capillary electrophoresis, the method comprising the following steps:

(a) applying an electric field between inlet and outlet ends of a separation capillary containing a source electrolyte solution, said field inducing an electroosmotic plug-like flow of said electrolyte through said separation capillary;

(b) series-coupling an electrically-conductive junction to said outlet end of said separation capillary such that by at least a downstream region of said electrically-conductive junction essentially zero axial incremental voltage from said electric field remains and said plug-like flow is converted to parabolic flow;

wherein electrolyte entering said electrically-conductive junction is subject to electroosmotic forces and to electrical forces, but electrolyte downstream from said downstream region of said electrically-conductive junction flows passively due to said electroosmotic forces; and (c) coupling flow detection means for detecting at least one parameter associated with flow of said electrolyte through said electrically-conductive junction;

wherein said flow detection means provides a real-time measure of electroosmotic flow through said separation capillary.

2. The method of claim 1, wherein at step (b) said electrically-conductive junction includes a flow conduit having an electrically-conducting wall coupled to ground potential, said wall being incapable of passing a bulk flow of said electrolyte solution.

3. The method of claim 1, wherein at step (c) said flow detection means is series-coupled to receive said parabolic flow from said electrically-conductive junction, and wherein at least one said parameter is selected from the group consisting of (i) streaming potential generated in said flow detection means, (ii) streaming current generated in said flow detection means, (iii) pressure differential generated along said flow detection means.

4. The method of claim 1, wherein at step (b), said electrically-conductive junction is selected from the group consisting of: (i) a porous glass junction, (ii) a junction fabricated from an ion-exchange polymer, (iii) a porous polymer junction, (iv) a junction fabricated from a conductive metal, (v) a junction fabricated from a sintered bed of glass particles, (vi) a junction fabricated from a sintered bed of silica particles, (vii) a junction fabricated by casting a solution of ion-exchange polymer over a fracture near said outlet end of said separation capillary, and (viii) a junction fabricated by casting a solution of porous polymer over a fracture near said outlet end of said separation capillary.

5. The method of claim 1, wherein at step (b), said electrically-conductive junction is selected from the group consisting of (i) an ion-exchange unit that includes a flow channel defined at least in part by an ion-exchange membrane being selectively permeable to ions of opposite charge to analyte ions of interest, but being impermeable to ions of like charge as analyte ions of interest, and (ii) an ion-impermeable unit that defines a flow channel and is impermeable to both cations and anions;

wherein electrolyte ions upstream of said channel have a flux proportional to $C_1 \cdot (\mu_e + \mu_{eo})$ where $C_1$ is upstream anion concentration in said source electrolyte solution, $\mu_e$ is electrolyte anion mobility, and $\mu_{eo}$ is electroosmotic mobility of said source electrolyte solution;

wherein electrolyte ions downstream of said channel have an equal flux proportional to $C_2 \cdot \mu_{eo}$, where $C_2$ is downstream anion electrolyte concentration; and wherein said flow detection means determines at least $C_2$ and from said $C_1$ and $C_2$ said real-time measure of electroosmotic flow through said separation capillary.

6. The method of claim 5, wherein step (c) includes providing a said electrically-conductive junction having an axial length sized to drop to zero said electric field by said downstream region, and contacting at least a portion of said electrically-conductive junction with a conductive solution that is at ground potential.

7. The method of claim 5, wherein at step (b), said electrically-conductive junction is an ion-exchange unit that preferentially exchanges an ion type selected from the group consisting of (i) anions, and (ii) cations.

8. The method of claim 5, wherein at step (b) said electrically-conductive junction is an ion-exchange unit that defines a cross-section selected from the group consisting of (i) a rectangle, (ii) a square, (iii) an oval, and (iv) a circle.

9. The method of claim 5, wherein at said step (b), said electrically-conductive junction is an ion-exchange unit that includes a membrane containing Nafion ™ material.

10. The method of claim 5, wherein at said step (b), said electrically-conductive junction is an ion-impermeable unit fabricated from palladium.

11. The method of claim 5, wherein at step (c) at least concentration $C_2$ is measured using an instrument selected from the group consisting of (i) a conductivity meter, and (ii) an ultraviolet absorbance detector.

12. The method of claim 1, including the further step of detecting analyte ions separated by said separation capillary, said step of detecting using at least one instrument selected from the group consisting of (i) an ultraviolet photometer, (ii) a fluorimeter, (iii) a conductivity meter, (iv) a suppressor followed by a conductivity detector, (v) and optical detector, (vi) a spectrophotometer, (vii) an amperometric detector, (viii) a potentiometric detector, and (ix) a mass spectrometer.

13. The method of claim 1, further including the step of providing feedback means for varying said source electroosmotic flow, said feedback means having an input coupled to an output of said flow detection means; wherein said feedback means controls electroosmotic flow rate of said source electrolyte through said separation capillary in real-time.

14. The method of claim 13, wherein an output of said feedback means is coupled to said separation capillary to at least one parameter selected from the group consisting of: (i) zeta-potential at said separation capillary inner wall, (ii) capillary inlet pressure, and (iii) capillary outlet pressure.

15. A system for real-time determination of electroosmotic flow rate during separation by capillary electrophoresis, the system comprising:

means for applying an electric field between inlet and outlet ends of a separation capillary containing a source electrolyte solution, said field inducing an electroosmotic plug-like flow of said electrolyte through said separation capillary;

an electrically-conductive junction series-coupled to said outlet end of said separation capillary such that by at least a downstream region of said electrically-conductive junction essentially zero axial incremental voltage from said electric field remains and said plug-like flow is converted to parabolic flow; wherein electrolyte entering said electrically-conductive junction is subject to electroosmotic forces and to electrical forces, but electrolyte downstream from said downstream region of said electrically-conductive junction flows passively due to said electroosmotic forces; and flow detection means for detecting at least one parameter associated with flow of said electrolyte through said electrically-conductive junction; wherein said flow detection means provides a real-time measure of electroosmotic flow through said separation capillary.

16. The system of claim 15, wherein said electrically-conductive junction includes a flow conduit having an electrically-conducting wall coupled to ground potential, said wall being incapable of passing a bulk flow of said electrolyte solution.

17. The system of claim 15, wherein said flow detection means is series-coupled to receive said parabolic flow from said electrically-conductive junction, and wherein said at least one parameter is selected from the group consisting of (i) streaming potential generated in said flow detection means, (ii) streaming current generated in said flow detection means, and (iii) pressure differential generated along said flow detection means.

18. The system of claim 15, wherein said electrically-conductive junction is selected from the group consisting of: (i) a porous glass junction, (ii) a junction fabricated from an ion-exchange polymer, (iii) a porous polymer junction, (iv) a junction fabricated from a conductive metal, (v) a junction fabricated from a sintered bed of glass particle, (vi) a junction fabricated from a sintered bed of silica particles, (vii) a junction fabricated by casting a solution of ion-exchange polymer over a fracture near said outlet end of said separation capillary, and (viii) a junction fabricated by casting a solution of porous polymer over a fracture near said outlet end of said separation capillary.

19. The system of claim 15, wherein said electrically-conductive junction is selected from the group consisting of (i) an ion-exchange unit that includes a flow channel defined at least in part by an ion-exchange membrane being selectively permeable to ions of opposite charge to analyte ions of interest, but being impermeable to ions of like charge as analyte ions of interest, and (ii) an ion-impermeable unit that includes a flow channel and is impermeable to both cations and anions;

wherein electrolyte ions upstream of said channel have a flux proportional to $C_1 \cdot (\mu_e + \mu y_{eo})$ where $C_1$ is upstream anion concentration in said source electrolyte solution, $\mu_e$ is electrolyte anion mobility, and $\mu_{eo}$ is electroosmotic mobility of said source electrolyte solution;

wherein electrolyte ions downstream of said channel have an equal flux proportional to $C_2 \cdot \mu_{eo}$, where $C_2$ is downstream anion electrolyte concentration; and wherein said flow detection means determines at least $C_2$ and from said $C_1$ and $C_2$ said real-time measure of electroosmotic flow through said separation capillary.

20. The system of claim 19, wherein said electrically-conductive junction has an axial length sized to drop to zero said electric field by said downstream region, and at least a portion of said electrically-conductive junction is at ground potential.

21. The system of claim 19, wherein said at least a portion of said electrically-conductive junction is coupled to said ground potential using a device selected from the group consisting of (i) coupling a conductive lead between said junction and ground potential, and (ii) by contacting said junction with a conductive solution that is at ground potential.

22. The system of claim 19, wherein said electrically-conductive junction defines a cross-section selected from the group consisting of (i) a rectangle, (ii) a square, (iii) an oval, and (iv) a circle.

23. The system of claim 19, wherein said electrically-conductive junction is an ion-exchange unit that preferentially exchanges an ion type selected from the group consisting of (i) anions, and (ii) cations.

24. The system of claim 23, wherein said ion-exchange unit includes a membrane containing Nafion ™ material.

25. The system of claim 19, wherein said electrically-conductive junction is an ion-impermeable unit fabricated from palladium.

26. The system of claim 15, wherein at least concentration $C_2$ is measured using an instrument selected from the group consisting of (i) a conductivity meter, and (ii) an ultraviolet absorbance detector.

27. The system of claim 15, further including means for detecting analyte ions separated by said separation capillary, said means-for detecting including at least one instrument selected from the group consisting of (i) an ultraviolet photometer, (ii) a fluorimeter, (iii) a conductivity meter, (iv) a suppressor followed by a conductivity detector, (v) and optical detector, (vi) a spectrophotometer, (vii) an amperometric detector, (viii) a potentiometric detector, and (ix) a mass spectrometer.

28. The system of claim 15, further feedback means for varying said source electroosmotic flow, said feedback means having an input coupled to an output of said flow detection means;

wherein said feedback means controls electroosmotic flow rate of said source electrolyte through said separation capillary in real-time.

29. The system of claim 28, wherein an output of said feedback means is coupled to said separation capillary to at least one parameter selected from the group consisting of: (i) zeta-potential at said separation capillary inner wall, (ii) capillary inlet pressure, and (iii) capillary outlet pressure.

* * * * *